US007001739B2

(12) United States Patent
Mirkov et al.

(10) Patent No.: US 7,001,739 B2
(45) Date of Patent: Feb. 21, 2006

(54) ISOLATION OF PROTEINS INVOLVED IN POSTTRANSCRIPTIONAL GENE SILENCING AND METHODS OF USE

(75) Inventors: T. Erik Mirkov, Harlingen, TX (US); Ivan L. Ingelbrecht, Jabbeke (BE)

(73) Assignee: The Texas A&M University System, College Station, TX (US)

( * ) Notice: Subject to any disclaimer, the term of this patent is extended or adjusted under 35 U.S.C. 154(b) by 462 days.

(21) Appl. No.: 10/226,715

(22) Filed: Aug. 23, 2002

(65) Prior Publication Data

US 2003/0099984 A1    May 29, 2003

Related U.S. Application Data

(60) Provisional application No. 60/314,863, filed on Aug. 24, 2001.

(51) Int. Cl.
*G01N 33/569* (2006.01)
*G01N 33/53* (2006.01)
*C12N 15/33* (2006.01)

(52) U.S. Cl. .................. 435/7.91; 435/7.31; 536/23.72
(58) Field of Classification Search .................... 435/6, 435/419, 468, 7.31, 7.4, 7.91, 7.8; 536/23.72; 800/278
See application file for complete search history.

(56) References Cited

U.S. PATENT DOCUMENTS

| 5,939,541 A | 8/1999 | Vance et al. ................ 536/24.1 |
| 6,040,496 A | 3/2000 | Law et al. ................... 800/280 |

OTHER PUBLICATIONS

Newberry et al., Biochem., 1999, vol. 38, pp. 10678-10690.*
Dagkessamanskaia et al., FEMS Microbiol. Lett., Jun. 2001, vol. 200, pp. 53-58.*
Anandalakshmi, Radhamani, "A Calmodulin-Related Protein that Suppresses Posttranscriptional Gene Silencing in Plants", Science, American Association for the Advancement of Science, vol. 290, No. 5489, pp. 142-144., Oct. 6, 2000.
Database Embl AF215815 , Geering, A.D. et al., "Genetic Diversity Among Banana Streak Virus Isolates from Australia". 2 pages, Jul. 18, 2000.
Geering, A.D. et al., "Genetic Diversity Among Banana Streak Virus Isolates from Australia", XP008017774, Phytopathology, vol. 90, No. 8, pp. 921-927, Aug. 2000.
Database Embl AJ001691.1, Kong, P., "Complete Nucleotide Sequence and Analysis of the Putative Polyprotein of Maize Dwarf Mosaic Virus Genomic RNA (Bulgarian Isolate)", 5 pages, May 6, 1998.
Kong, P., "Complete Nucleotide Sequence and Analysis of the Putative Polyprotein of Maize Dwarf Mosaic Virus Genomic RNA (Bulgarian Isolate)", Archives of Virology, vol. 143, No. 9, pp. 1791-1799, 1998.
Mallory, T.H., et al., "Suppression of RNA Silencing in Plants", Phytopathology, vol. 91, No. 6 Supplement, 1 page, Abstract, Jun. 2001.
Matzke, Marjori et al., "RNA-based Silencing Strategies in Plants", Current Opinion in Genetics & Development, vol. 11, No. 2, pp. 221-227, Apr. 2001.
Mirkov, T.E. et al., "Monocot Host Proteins that Interact with a Viral Suppressor of Gene Silencing", Phytopathology, vol. 91, No. 6 Supplement, 1 page, Abstract, Jun. 2001.
Chuang, et al., "Specific and Heritable Genetic Interference by Double-Stranded RNA in Arabidopsis Thaliana", PNAS, vol. 97 No. 9, pp. 4985-4990, Apr. 25, 2000.
Anandalakshmi, Radhamani et al., "A viral suppressor of gene silencing in plants," Proc. Natl. Acad. SCi. USA vol. 95, pp. 13079-13084, Oct. 1998.
Atreya, Chintamani D. et al., "Mutational analysis of the helper component-proteinase gene of potyvirus: Effects of amino acid substitutions, deletions, and gene replacement on virulence and aphid transmissibility," Proc. Natl. Acad. Sci. USA vol. 90, pp. 11919-11923, Dec. 1993.
Brigneti, Gianinna et al., "Viral pathogenicity determinants are suppressors of transgene silencing in *Nicotiana benthamiana*," The EMBO Journal vol. 17 No. 22, pp. 6739-6746, 1998.
Carrington, James C. et al., "Expression of potyviral polyproteins in transgenic plants reveals three proteolytic activities required for complete processing," The EMBO Journal, vol. 9, No. 5, pp. 1347-1353, 1990.
Chuang, Chiou-Fen et al., "Specific and heritable genetic interference by double-stranded RNA in *Arabidopsis thaliana*," PNAS vol. 97 No. 9, pp. 4985-4990, Apr. 25, 2000.
Cogoni, Carlo et al., "Conservation of transgene-induced post-transcriptional gene silencing in plants and fungi," Trends in Plant Science Reviews vol. 2, No. 11, pp. 438-443, Nov. 1997.

(Continued)

*Primary Examiner*—Ashwin Mehta
(74) *Attorney, Agent, or Firm*—Baker Botts L.L.P.

(57) ABSTRACT

The present invention includes a method for detecting and isolating sugarcane proteins that interact with the HC-Pro and P1 proteins of SrMV and other proteins involved in gene silencing, particularly in sugarcane. The method uses a two hybrid assay with an HC-Pro, P1, or other silencing-related protein-containing bait protein and a prey protein containing a polypeptide encoded by a DNA molecule in a cDNA library. The method also includes identification of false positives through reverse two-hybrid assays and using in vitro techniques such as farwestern blots or pull down assays where plant physiological conditions may be replicated. Finally, interactions may be confirmed in planta. Some novel proteins used in and discovered using the these methods are also identified. Methods of using viral and plant proteins to regulate silencing in plants such as sugarcane are also discussed.

9 Claims, 21 Drawing Sheets

OTHER PUBLICATIONS

Cogoni, Carlo et al., "Gene silencing in *Neurospora crassa* requires a protein homologous to RNA-dependent RNA polymerase," Nature vol. 399, pp. 166-169, May 13, 1999.

Cogoni, Carlo et al., "Isolation of quelling-defective (*qde*) mutants impaired in posttranscriptional transgene-induced gene silencing in *Neurospora crassa*," Proc. Natl. Acad. Sci. USA vol. 94, pp. 10233-10238, Sep. 1997.

Cogoni, Carlo et al., "Posttranscriptional Gene Silencing in *Neurospora* by a RecQ DNA Helicase," Science vol. 286, pp. 2342-2344, Dec. 17, 1999.

Covey, Simon N. et al., "Plants combat infection by gene silencing," Nature vol. 385 pp. 781-782, Feb. 27, 1997.

Cronin, Stephen et al., "Long-Distance Movement Factor: A Transport Function of the Potyvirus Helper Component Proteinase," The Plant Cell vol. 7, pp. 549-559, May 1995.

Dalmay, Tamas et al., "An RNA-Depdendent RNA Polymerase Gene in *Arabidopsis* is Required for Post-transcriptional Gene Silencing Mediated by a Transgene but Not by a Virus," Cell, vol. 101, pp. 543-553, May 26, 2000.

Dehio, Christoph et al., "Identification of plant genetic loci involved in a posttranscriptional mechanism for meiotically reversible transgene silencing," Proc. Natl. Acad. Sci. USA vol. 91, pp. 5538-5542, Jun. 1994.

Depicker, Ann et al., "Post-transcriptional gene silencing in plants," Current Opinion in Cell Biology 1997, vol. 9, pp. 373-382, 1997.

Elmayan, Taline et al. "Arabidopsis Mutants Impaired in Cosuppression," The Plant Cell, vol. 10, pp. 1747-1757, Oct. 1998.

Fields, Stanley et al., "A novel genetic system to detect protein-protein interactions," Nature vol. 340 pp. 245-246, Jul. 20, 1989.

Gindullis, Frank et al., "MAF1, a Novel Plant Protein Interacting with Matrix Attachment Region Binding Protein MFP1, Is Located at the Nuclear Envelope," The Plant Cell, vol. 11, pp. 1755-1767, Sep. 1999.

Guo, Deyin et al., "Self-association and mapping of interaction domains of helper component-proteinase of potato A potyvirus," Journal of General Virology (1999), vol. 80, pp. 1127-1131, 1999.

Hamilton, Andrew J. et al., "A Species of Small Antisense RNA in Posttranscriptional Gene Silencing in Plants," Science vol. 286 pp. 950-952, Oct. 29, 1999.

Ingelbrecht, Ivan et al., "Posttranscriptional silencing of reporter transgenes in tobacco correlates with DNA methylation," Proc. Natl. Acad. Sci. USA vol. 91, pp. 10502-10506, Oct. 1994.

Ingelbrecht, Ivan L. et al., "Posttranscriptional Gene Silencing in Transgenic Sugarcane. Dissection of Homology-Dependent Virus Resistance in a Monocot That Has a Complex Polyploid Genome," Plant Physiology, vol. 119, pp. 1187-1197, Apr. 1999.

Kasschau, Kristin D. et al., "A Counterdefensive Strategy of Plant Viruses: Suppression of Posttranscriptional Gene Silencing," Cell vol. 95, pp. 461-470, Nov. 13, 1998.

Kasschau, Kristin D. et al., "Genome Amplification and Long-Distance Movement Functions Associated with the Central Domain of Tobacco Etch Potyvirus Helper Component-Proteinase," Virology vol. 228, Article No. VY968368, pp. 251-262, 1997.

Kennerdell, Jason R. et al., "Use of dsRNA-Mediated Genetic Interference to Demonstrate that *frizzled* and *frizzled* 2 Act in the Wingless Pathway," Cell vol. 95, pp. 1017-1026, Dec. 23, 1998.

Ketting, Rene F. et al., "mut-7 of *C. elegans*, Required for Transposon Silencing and RNA Interference, Is a Homolog of WErner Syndrome Helicase and RNaseD," Cell vol. 99, pp. 133-141, Oct. 15, 1999.

Kleiman, Frida E. et al., "Functional Interaction of BRCA1-Associated BARD1 with Polyadenylation Factor CstF-50," Science vol. 285, pp. 1576-1579, Sep. 3, 1999.

Kohalmi, Susanne E. et al., "Identification and characterization of protein interactions using the yeast 2-hybrid system," Plant Molecular Biology Manuari, vol. M1, pp. 1-30, 1998.

Kumagai, M.H. et al., "Cytoplasmic inhibition of carotenoid biosynthesis with virus-derived RNA," Proc. Natl. Acad. Sci. USA vol. 92, pp. 1679-1683, Feb. 1995.

Kumpatla, Siva P. et al., "Genome intruder scanning and modulation systems and transgene silencing," Trends in Plant Science, vol. 3, No. 3, pp. 97-104, Mar. 1998.

Lindbo, John A. et al., "Induction of a Highly Specific Antiviral State in Transgenic Plants: Implications for Regulation of Gene Expression and Virus Resistance," The Plant Cell, vol. 5, pp. 1749-1759, Dec. 1993.

Matzke, M.A. et al., "Epigenetic silencing of plant transgenes as a consequence of diverse cellular defence resonses," CMLS, Cell. Mol. Life Sci. vol. 54 (1998), pp. 94-103, 1998.

Misquitta, Leonie et al., "Targeted disruption of gene function in *Drosophila* by RNA interference (RNA-i): A role for *nautilus* in embryonic somatic muscle formation," Proc. Natl. Acad. Sci. USA vol. 96, pp. 1451-1456, Feb. 1999.

Montgomery, Mary K. et al., "Double-stranded RNA as a mediator in sequence-specific genetic silencing and co-supression," TIG Jul. 1998 vol. 14 No. 7 pp. 255-258, Jul. 1998.

Mourrain, Philippe et al., "*Arabidopsis SGS2* and *SGS3* Genes Are Required for Posttranscriptional Gene Silencing and Natural Virus Resistance," Cell, vol. 101, pp. 533-542, May 26, 2000.

Napoli, Carolyn et al., "Introduction of a Chimeric Chalcone Synthase Gene into Petunia Results in REversible Co-Suppression of Homologous Genes in trans," The Plant Cell, vol. 2, pp. 279-289, Apr. 1990.

Palauqui, Jean-Christophe et al., "Systemic acquired silencing: transgene-specific post-transcriptional silencing is transmitted by grafting from silenced stocks to non-silenced scions," The EMBO Journal vol. 16 No. 15 pp 4738-4745, 1997.

Pruss, Gail et al., "Plant Viral Synergism: The Potyviral Genome Encodes a Broad-Range Pathogenicity Enhancer That Transactivates Replication of Heterologous Viruses," The Plant Cell, vol. 9, pp. 859-868, Jun. 1997.

Ratcliff, Frank et al., "A Similarity Between Viral Defense and Gene Silencing in Plants," Science vol. 276, pp. 1558-1560, Jun. 6, 1997.

Revers, Frederic et al., "New Advances in Understanding the Molecular Biology of Plant/Potyvirus Interactions," MPMI, vol. 12, No. 5, pp. 367-376, 1999.

Ruiz, M. Teresa et al., "Initiation and Maintenance of Virus-Induced Gene Silencing," The Plant cell, vol. 10, pp. 937-946, Jun. 1998.

Sanchez Alvarado, Alejandro et al., "Double-stranded RNA specifically disrupts gene expression during planarian regeneration," Proc. Natl. Acad. Sci. USA vol. 96, pp. 5049-5054, Apr. 1999.

Schiebel, Winfried et al., "Isolation of an RNA-Directed RNA Plymerase-Specific cDNA Clone from Tomato," The Plant Cell, vol. 10, pp. 2087-2101, Dec. 1998.

Sehnke, Paul C. et al., "Consummating Signal Transduction: The Role of 14-3-3 Proteins in the Completion of Signal-Induced Transitions in Protein Activity," The Plant Cell, Supplement 2002, pp. S339-S354, 2002.

Sharp, Phillip A., "RNAi and double-strand RNA," Genes & Development vol. 13, pp. 139-141, 1999.

Shukla, Dharma D. et al., "The Sugarcane Mosaic Virus Subgroup," The Potyviridae, CABI Chapter 11 pp. 360-371, 1994.

Smith, Neil A. et al., "Total silencing by intronspliced hairpin RNAs," Nature vol. 407 pp. 319-320, Sep. 21, 2000.

Tabara, Hiroaki et al., "The rde-1 Gene, RNA Interference, and Transposon Silencing in C. elegans," vol. 99 pp. 123-132, Oct. 15, 1999.

Thombury, David W. et al., "Purification and Characterization of Potyvirus Helper Component," Virology vol. 144, pp. 260-267, Mar. 4, 1985.

Urcuqui-Inchima, Silvio et al., "Potyvirus Helper Component-Proteinase Self-Interaction in the Yeast Two-Hybrid System and Delineation of the Interaction Domain Involved," Virology. 258, pp. 95-99, 1999.

van den Boogaart, Tom et al., "Can We Explain RNA-Mediated Virus Resistance by Homology-Dependent Gene Silencing?,"MPMI vol. 11, No. 7, pp. 717-723, 1998.

van der Krol, Alexander R. et al., "Flavonoid Genes in Petunia: Addition of a Limited Number of Gene Coples May Lead to a Suppression of gene Expression," The Plant Cell, vol. 2, pp. 291-299, Apr. 1990.

Vance, Vicki et al., "RNA Silencing in Plants-Defense and Counter defense," Science vol. 292 pp. 2277-2280, Jun. 22, 2001.

Voinnet, Olivier et al., "Suppression of gene silencing: A general strategy used by diverse DNA and RNA viruses of Plants," PNAS vol. 96, No. 24, pp. 14147-14152, Nov. 23, 1999.

Walhout, Alberta J.M. et al., "Protein Interaction Mapping in C. elegans Using Proteins Involved in Vulval Development," Science vol. 287, pp 116-122, Jan. 7, 2000.

Waterhouse, Peter M. et al., "Virus resistance and gene silencing in plants can be induced by simultaneous expression of sense and antisense RNA," Proc. Natl. Acad. Sci. USA, vol. 95, pp. 13959-13964, Nov. 1998.

Yang, Z.N. et al., "Sequence and Relationships of Sugarcane Mosaic and Sorghum Mosaic Virus Strains and Development of RT-PCR-Based RFLPs for Strain Discrimination," Phytopathology vol. 87, No. 9, pp. 932-939, May 12, 1997.

* cited by examiner gaattcgccc ttatttcagc catggcagga gcatggaaca ctgtgactta caagtggagg    60
ccgaatttgg acaacgcaag agatgttcga aaagtgatgg aacattttgc agcaaagcac   120
caagtttatg atgcaaagcg tgcagcagag cataacagta gaatccttcg caggactttt   180
gtacaagaaa ttgcaaaagc acctgaagag aagacttcat acaaacctca ggtgtgggtc   240
gaaaaacaag ataacaatcc aacgatccat ctacactatg ttagattcaa aaacaaggag   300
aaaaagatat tacccgagat cactccagga tcggtcgcaa agttaacgcg acggatactt   360
gagctcagca aaactacaaa gcttgaagtt gaactcattg gtaagaaaag acgcaaatcg   420
actaaactag caatcaaaag gcgcagaaac agagagtatt tgcattgtga aactagacac   480
gaaacaaaca aatttaagcg cgttgacatc aacatagaac gacactggtt tccacttgtg   540
aagaagattt caaagtgcta tagtcacata tcaccaagaa tgtacaaaaa catgagcaaa   600
ggcgacagtg ggttaacatt catccagaat ggtgagttat ttataatccg aggaaaacga   660
gatggcgtcc tacttaatag tatcaccaat gaaactcgaa ttaatgaaat aacttatttt   720
agcgatgctc aggcgaacga cttctggcga ggttacacag atcatatggt cgaaaatagg   780
ttaatttcta caactcatac agaacacata cccacaataa atttagagaa gtgtggaaag   840
aggatggcat tgttagagat attgtttcac tccacattca aaattacgtg taagcactgt   900
aacaatgacg atcttgaact atcggatgat gagtttggag aaagactata taagaactta   960
atcagaattg aagaaaagca aaagaatat ttagctgaag atcaaaagct taagcgaatg  1020
atatcctttc tgaaggatag atgcaatcca aaatttgagc atttaccatt attatggcag  1080
gtcgctgaaa caattggaca ttacactgat aatcaagcaa aacagatcct tgaagttaat  1140
gaagcgctca taaagtgaa cactctttct gttgaagatg cagtcaaagc tagcgcatcg  1200
ttgctagaga tttcaagatg gtacaagaat aggaaagaat catcgaaaga aggtacactt  1260
agtacattca ggaataaaat ttcacctaaa agtactatta atacagcact gatgtgtgat  1320
aatcagctcg atacaaatgg taacttccta tggggaaaga gagaatatca tgccaagcga  1380
ttctttacaa actattttga agctgttgat ccaaaagaca cgtatgaaaa gcatgttact  1440
cggttcaatc caaatggtca acgcaaactt tcgattggaa aactagttat cccattagac  1500
ttccagaaga ttcgtgaatc atttataggt gttcaagttc aaaaacaagc aattagtaga  1560
gcgtgcttaa gtaaaatcga aaataattac atatacccct gctgttgtgt aactacagaa  1620
tttggtcaac cggtttattc agagatcatt ccaccaacta aaggtcatat tactattgga  1680
aattcgaccg acccaaaaat tgtggattg cctaattccg acccaccaat gatgtacata  1740
gcgaaagatg gttattgtta tttgaatata tttttagctg ctctgataaa cgtcaatgaa  1800
gattcagcaa aagattacac aaagttttg cgtgatgaac taattgaaag acttggaaag  1860
tggccaaaac tcaaagacgt ggcgacagca tgttatgcat tatcagtaat gtttccagaa  1920
attaagaacg cggagcttcc acaaatacta gtggaccacg aacataaaac catgcatgtg  1980
atagattcgt acggatctct cagtgttggc ttccacatac tcaaagcgaa cacaatagga  2040
caattaatca aaatgcaata tgaatccatg gaaagtgaaa tgagagagta tgtagtcggt  2100
tag                                                                 2103
(SEQ.ID.NO. 1)

Figure 1A

MAGAWNTVTY KWRPNLDNAR DVRKVMEHFA AKHQVYDAKR AAEHNSRILR RTFVQEIAKA    60
PEEKTSYKPQ VWVEKQDNNP TIHLHYVRFK NKEKKILPEI TPGSVAKLTR RILELSKTTK    120
LEVELIGKKR RKSTKLAIKR RRNREYLHCE TRHETNKFKR VDINIERHWF PLVKKISKCY    180
SHISPRMYKN MSKGDSGLTF IQNGELFIIR GKRDGVLLNS ITNETRINEI TYFSDAQAND    240
FWRGYTDHMV ENRLISTTHT EHIPTINLEK CGKRMALLEI LFHSTFKITC KHCNNDDLEL    300
SDDEFGERLY KNLIRIEEKQ KEYLAEDQKL KRMISFLKDR CNPKFEHLPL LWQVAETIGH    360
YTDNQAKQIL EVNEALIKVN TLSVEDAVKA SASLLEISRW YKNRKESSKE GTLSTFRNKI    420
SPKSTINTAL MCDNQLDTNG NFLWGKREYH AKRFFTNYFE AVDPKDTYEK HVTRFNPNGQ    480
RKLSIGKLVI PLDFQKIRES FIGVQVQKQA ISRACLSKIE NNYIYPCCCV TTEFGQPVYS    540
EIIPPTKGHI TIGNSTDPKI VDLPNSDPPM MYIAKDGYCY LNIFLAALIN VNEDSAKDYT    600
KFLRDELIER LGKWPKLKDV ATACYALSVM FPEIKNAELP QILVDHEHKT MHVIDSYGSL    660
SVGFHILKAN TIGQLIKMQY ESMESEMREY VVGZ                              694
(SEQ.ID.NO 2)

Figure 1B ggccattatg gccggggaga acactgtatg aagaacatgg ccgcttctta tagtcaagac   60
gcgcagctcg atctcgtact tcctgacgct cccgtcgatg ctagcgcgtc tcgttctgaa   120
cattcatctc agcttgctag ctctaactgg agatctgtga ttcaaaactc cccacctgat   180
ctcctatgcg gatgcggtag accggcaatt aggcgcacgg cagagactgc gaagaacaat   240
ggccgcatct ttcgcacgtg tccggcgtgc aaaatatgga tttggcagga tctgctggac   300
agctatgtga atgctttgat aagctactgt cgtgatgcct ccattgattc ccttcagtca   360
gagcttgaat ctagccgttt attaatttcc gagaagcagg cacagatttc acgtttggag   420
aaacaattgg agacgctgca gccacttatc tcaaaatata ctgaacaatc tcgcagcatt   480
gctcaggcct ccattccatc atcacttttt ttcttggaag cctgcagtct ccgacatcag   540
cggcggaggg tgaatgaaaa tcaaggaggg gctaatttca aaagaagcta ctggagcgat   600
taaagcttcg gttaaaaata agcaagaatc taacacccag agcacaaatt ccatgagctg   660
gcttttttt gggacaccct ttcattttc atcaaaaaag ggggggcacc cccagtttcc   720
tccaaaaggc tccccctgtc cgacatcata ggtgatgtga ttacccaaaa acaggttgtc   780
ccgcttgctg actcgatgcc aaatttggat tcaatgctgc tcctgttgtt ttaacaatca   840
atcattttga ctaaaagcat tccccttaaa attgttgtta aatttattgt caaacttatt   900
accgcaaagt ccgttggcag gtaatccccc ccttttt         937
(SEQ.ID.NO. 3)

Figure 6A

GHYGRGEHCM KNMAASYSQD AQLDLVLPDA PVDASASRSE HSSQLASSNW RSVIQNSPPD   60
LLCGCGRPAI RRTAETAKNN GRIFRTCPAC KIWIWQDLLD SYVNALISYC RDASIDSLQS   120
ELESSRLLIS EKQAQISRLE KQLETLQPLI SKYTEQSRSI AQASIPSSLF FLEACSLRHQ   180
RRRVNENQGG ANFKRSYWSD         200
(SEQ.ID.NO.4)

Figure 6B gaattcggcc attatggccg gggcatgtgc agtgaatgcg ccaaggtcct gaggtaccaa  60
accactcggt gccccatctg caggcagcct gttgagcgtc tcctcgagat caaagtgagc  120
aacaaatctg aagagcagca gcagacgccc caatcgccgc cgctcccagc cccagctctg  180
cagcaggaag aggtgtagcc gtgattaaag tcagttctga gacattatat ggaactagtt  240
tgcggccttc aggcctttcc ctaaaggttt gttctctcat ctgagcaacg gggaatgtaa  300
ccggtacttt acctttagcc tatgtaagct tctggcatcg catggctttg ccgacctctg  360
ctgtacctgc ttatctggag gtcggagacc aagatgccaa ggaaagtgtg taccgtatat  420
taaaaaaaaa aaaaaaaaaa aaaaaaaa                                    449
(SEQ.ID.NO. 5)

Figure 7A

EFGHYGRGMC SECAKVLRYQ TTRCPICRQP VERLLEIKVS NKSEEQQQTP QSPPLPAPAL  60
QQEEVZPZLK SVLRHYMELV CGLQAFPZRF VLSSEQRGMZ PVLYLZPMZA SGIAWLCRPL 120
LYLLIWRSET KMPRKVCTVY ZKKKKKKKK                                  149
(SEQ.ID.NO. 6)

Figure 7B gaattcggcc attatggccg ggaccaggaa ctccaggaat cagatgacaa ctcggggtat    60
agagctcctg aagtgaccat gtccggtcag tattctcaaa agagtgatgt ttacagcttt    120
ggtgtcgtca tgcttgagct actgactgga cagaaagcat ttgacagctc tcgggcaagg    180
tcccagcaat cactagtccg gtgggcttca ccgcagctgc acgacatcga ctcgctagat    240
cagatggttg atccaaacctt agaggggctg taccatgcga aatcactctc tcggttcgca    300
gacgcaatcg ctctctgtgt ccagcctgaa ccagaattca ggccaccaat gtcggaggtc    360
gtccagtcac tggtccgtct tgtgcagcga gcaagcatgg ggacagcact aagcagcgag    420
tggaattctt gccagttcga tgaatctggt gatcacacgc tctaggggaa aatgatgtgt    480
atttcctaga gagtctgatg aggaactata gaaggctcac aagtcataga aacttgcagc    540
ttggcattgt tgtgagttgt gacggtgtga catgtgccag tgtcaggtga aatgtgactt    600
ttacctatgc cattttactg agagtctgct gcaacctgaa gtaggggtga aaagaaagtt    660
ccttctttaa aaatatatat ggttcattcg gacgtgtata tgaatatctt ttgaagacaa    720
tcaactttct gatttcgtct ctgatcgctg tccaaaaatt atcagggaag atgtagcact    780
agtcctgcca cagaattagt catctgtata tcctcagaaa tccgaaccat atccaggaaa    840
catcaacaga ggacacgtcc acatattcga ac                                  872
(SEQ.ID.NO. 7)

Figure 8A

EFGHYGRDQE LQESDDNSGY RAPEVTMSGQ YSQKSDVYSF GVVMLELLTG QKAFDSSRAR    60
SQQSLVRWAS PQLHDIDSLD QMVDPTLEGL YHAKSLSRFA DAIALCVQPE PEFRPPMSEV    120
VQSLVRLVQR ASMGTALSSE WNSCQFDESG DHTLZGKMMC ISZRVZZGTI EGSQVIETCS    180
LALLZVVTVZ HVPVSGEMZL LPMPFYZESA ATZSRGEKKV PSLKIYMVHS DVYMNIFZRQ    240
STFZFRLZSL SKNYQGRCST SPATELVICI SSEIRTISRK HQQRTRPHIR              290
(SEQ.ID.NO. 8)

Figure 8B

```
gaattcggcc attatggccg gggaccgcag ttcccccgac cacaccgttc cgccgcgcac    60
agaggccagc cccgcgccag gagtaagttt gttcttttta acaatatgtc gagggaggag   120
aatgtttaca tggccaagct ggctgagcag gccgaaaggt atgaggagat ggttgagtat   180
atggagaagg tggctaagac tgtagatgtt gaagagctca ctgtggagga gcgtaacctc   240
ctgtctgtcg catacaagaa tgtgattggg gctcgccgtg cttcatggcg cattgtctct   300
tccattgaac agaaggagga gtcccgtaag aacgaagagc atgtgaacct tatcaaggaa   360
taccgcggga agattgaggc tgaactgagc aacatctgtg atggcatcct gaaactgctt   420
gactcccacc tagtgccttc ctctactgct gctgaatcaa aggtcttcta cctcaagatg   480
aagggtgact atcacaggta tcttgcggaa tttaagactg gtgctgagag gaaggaatct   540
gctgagagca caatggtagc ctacaaggct gctcaggaca ttgctctggc tgagctggca   600
cctacacatc cgataaggct tgggcttgct cttaacttct cagtgttcta ttatgagatt   660
ctgaactccc cagacaaagc ttgcaacctt gcaaagcagg cgtttgatga agctatctct   720
gagttagaca cccttgggga ggagtcatac aaagatagca ctctgatcat gcagctcctg   780
agggacaact tgaccctttg gacctctgac ctcacggagg atggtgctga tgagggcaaa   840
gaagcctcaa aaggtgatgc tggcgaggga cagtaatctt cggagagggc atgttgttcc   900
agcctggttt tagatgctct atgctgtcga agctgtgccg tgccattatt gtagcagatt   960
tcctctcccc ctcacttcat ttgcctcata ttagtaggct ggtagtggtc gaattagttc  1020
ccattgcttt gtgttgcagc tagttggcac taggtccgtg tggactggta ttgttcccct  1080
ggatttgaca agcatgtcct gtggtcgctc tagcgtttta ttgagctttg aagcctcgat  1140
t                                                                 1141
(SEQ.ID.NO. 9)
```

Figure 9A

```
EFGHYGRGPQ FPRPHRSAAH RGQPRARSKF VLFNNMSREE NVYMAKLAEQ AERYEEMVEY    60
MEKVAKTVDV EELTVEERNL LSVAYKNVIG ARRASWRIVS SIEQKEESRK NEEHVNLIKE   120
YRGKIEAELS NICDGILKLL DSHLVPSSTA AESKVFYLKM KGDYHRYLAE FKTGAERKES   180
AESTMVAYKA AQDIALAELA PTHPIRLGLA LNFSVFYYEI LNSPDKACNL AKQAFDEAIS   240
ELDTLGEESY KDSTLIMQLL RDNLTLWTSD LTEDGADEGK EASKGDAGEG QZSSERACCS   300
SLVLDALCCR SCAVPLLZQI SSPPHFICLI LVGWZWSNZF PLLCVAASWH ZVRVDWYCSP   360
GFDKHVLWSL ZRFIELZSLD         380
(SEQ.ID.NO. 10)
```

Figure 9B

```
gaattcggcc attatggccg ggctgttcaa gctggaccgt tatatggtat gggacaccat    60
ggatcttcca ccacaattgc ttatggcggt gcatacttgc catattcttc ctcaactgga   120
caatcgagca ataatcatca agagcatgga tttcctgagc ggccagggca gcctgagtgt   180
caatatttta tgaggactgg aggttgcaaa tttggaacta tgtgtaaata taaccatcct   240
cgagattgga gcactcctaa gtccaactac atgttcagtc atctctgcct tccacttcgt   300
ccgggtgctc agccttgtgc gtactatgca caaaatggat attgcagata tggagttgca   360
tgcaaatatg atcacccaat gggtacacta ggctacagtt catctgcttt accccctatct  420
gacatgccaa ttgctcccta ccctatcggc ttctctgttg ccacgttggc tccatcttca   480
tcttccccag aatatatttc aaccaaagat ccatcaatca accaagtagc atcaccagtg   540
cagcacccga acatgttgga acaatcttgc caaaaggggt ttcccttcgg atccattatg   600
cgaactcaac ttctacaagt gtcggcagtt caagcctggg gggcgctgat tttctgactg   660
ggggatgatc cttaacacaa atttctatac ttgaacagtt tgaagccttc aaggaataaa   720
aactggggcc ttgaaaaacc gggaggggtt cttcccaaat aaaactgtgg tcaacactca   780
tcctgaattg gtttcctatt caaacggaag aggtttagga gtcacattg                829
(SEQ.ID.NO. 11)
```

Figure 10A

```
EFGHYGRAVQ AGPLYGMGHH GSSTTIAYGG AYLPYSSSTG QSSNNHQEHG FPERPGQPEC   60
QYFMRTGGCK FGTMCKYNHP RDWSTPKSNY MFSHLCLPLR PGAQPCAYYA QNGYCRYGVA  120
CKYDHPMGTL GYSSSALPLS DMPIAPYPIG FSVATLAPSS SSPEYISTKD PSINQVASPV  180
QHPNMLEQSC QKGFPFGSIM RTQLLQVSAV QAWGALIFZL GDDPZHKFLY LNSLKPSRNK  240
NWGLEKPGGV LPKZNCGQHS SZIGFLFKRK RFRSHI                            276
(SEQ.ID.NO. 12)
```

Figure 10B

SEQUENCE LISTING

```
<160> NUMBER OF SEQ ID NOS: 12

<210> SEQ ID NO 1
<211> LENGTH: 2103
<212> TYPE: DNA
<213> ORGANISM: Sorghum mosaic virus strain H
```

<400> SEQUENCE: 1

```
gaattcgccc ttatttcagc catggcagga gcatggaaca ctgtgactta caagtggagg      60
ccgaatttgg acaacgcaag agatgttcga aaagtgatgg aacattttgc agcaaagcac     120
caagtttatg atgcaaagcg tgcagcagag cataacagta gaatccttcg caggactttt     180
gtacaagaaa ttgcaaaagc acctgaagag aagacttcat acaaacctca ggtgtgggtc     240
gaaaaacaag ataacaatcc aacgatccat ctacactatg ttagattcaa aaacaaggag     300
aaaaagatat tacccgagat cactccagga tcggtcgcaa agttaacgcg acggatactt     360
gagctcagca aaactacaaa gcttgaagtt gaactcattg gtaagaaaag acgcaaatcg     420
actaaactag caatcaaaag gcgcagaaac agagagtatt tgcattgtga aactagacac     480
gaaacaaaca aatttaagcg cgttgacatc aacatagaac gacactggtt tccacttgtg     540
aagaagattt caaagtgcta tagtcacata tcaccaagaa tgtacaaaaa catgagcaaa     600
ggcgacagtg ggttaacatt catccagaat ggtgagttat ttataatccg aggaaaacga     660
gatggcgtcc tacttaatag tatcaccaat gaaactcgaa ttaatgaaat aacttatttt     720
agcgatgctc aggcgaacga cttctggcga ggttacacag atcatatggt cgaaaatagg     780
ttaatttcta caactcatac agaacacata cccacaataa atttagagaa gtgtggaaag     840
aggatggcat tgttagagat attgtttcac tccacattca aaattacgtg taagcactgt     900
aacaatgacg atcttgaact atcggatgat gagtttggag aaagactata agaactta       960
atcagaattg aagaaaagca aaagaatat ttagctgaag atcaaaagct taagcgaatg    1020
atatccttc tgaaggatag atgcaatcca aaatttgagc atttaccatt attatggcag   1080
gtcgctgaaa caattggaca ttacactgat aatcaagcaa aacagatcct tgaagttaat    1140
gaagcgctca taaaagtgaa cactctttct gttgaagatg cagtcaaagc tagcgcatcg    1200
ttgctagaga tttcaagatg gtacaagaat aggaaagaat catcgaaaga aggtacactt    1260
agtacattca ggaataaaat ttcacctaaa agtactatta atacagcact gatgtgtgat    1320
aatcagctcg atacaaatgg taacttccta tggggaaaga gagaatatca tgccaagcga    1380
ttctttacaa actatttga agctgttgat ccaaaagaca cgtatgaaaa gcatgttact    1440
cggttcaatc caaatggtca acgcaaactt tcgattggaa aactagttat cccattagac    1500
ttccagaaga ttcgtgaatc atttataggt gttcaagttc aaaaacaagc aattagtaga    1560
gcgtgcttaa gtaaaatcga aataattac atatacccctt gctgttgtgt aactacagaa    1620
tttggtcaac cggtttattc agagatcatt ccaccaacta aaggtcatat tactattgga    1680
aattcgaccg acccaaaaat tgtggatttg cctaattccg acccaccaat gatgtacata    1740
gcgaaagatg gttattgtta ttgaatata ttttagctg ctctgataaa cgtcaatgaa    1800
gattcagcaa aagattacac aaagtttttg cgtgatgaac taattgaaag acttggaaag    1860
tggccaaaac tcaaagacgt ggcgacagca tgttatgcat tatcagtaat gtttccagaa    1920
attaagaacg cggagcttcc acaaatacta gtggaccacg aacataaaac catgcatgtg    1980
atagattcgt acggatctct cagtgttggc ttccacatac tcaaagcgaa cacaatagga    2040
caattaatca aaatgcaata tgaatccatg gaaagtgaaa tgagagagta tgtagtcggt    2100
tag                                                                  2103
```

<210> SEQ ID NO 2
<211> LENGTH: 694
<212> TYPE: PRT
<213> ORGANISM: Sorghum mosaic virus strain H

<400> SEQUENCE: 2

```
Met Ala Gly Ala Trp Asn Thr Val Thr Tyr Lys Trp Arg Pro Asn Leu
  1               5                  10                  15
Asp Asn Ala Arg Asp Val Arg Lys Val Met Glu His Phe Ala Ala Lys
             20                  25                  30
His Gln Val Tyr Asp Ala Lys Arg Ala Ala Glu His Asn Ser Arg Ile
         35                  40                  45
Leu Arg Arg Thr Phe Val Gln Glu Ile Ala Lys Ala Pro Glu Glu Lys
 50                  55                  60
Thr Ser Tyr Lys Pro Gln Val Trp Val Glu Lys Gln Asp Asn Asn Pro
 65                  70                  75                  80
Thr Ile His Leu His Tyr Val Arg Phe Lys Asn Lys Glu Lys Lys Ile
                 85                  90                  95
Leu Pro Glu Ile Thr Pro Gly Ser Val Ala Lys Leu Thr Arg Arg Ile
            100                 105                 110
Leu Glu Leu Ser Lys Thr Thr Lys Leu Glu Val Glu Leu Ile Gly Lys
        115                 120                 125
Lys Arg Arg Lys Ser Thr Lys Leu Ala Ile Lys Arg Arg Arg Asn Arg
130                 135                 140
Glu Tyr Leu His Cys Glu Thr Arg His Glu Thr Asn Lys Phe Lys Arg
145                 150                 155                 160
Val Asp Ile Asn Ile Glu Arg His Trp Phe Pro Leu Val Lys Lys Ile
                165                 170                 175
Ser Lys Cys Tyr Ser His Ile Ser Pro Arg Met Tyr Lys Asn Met Ser
            180                 185                 190
Lys Gly Asp Ser Gly Leu Thr Phe Ile Gln Asn Gly Glu Leu Phe Ile
        195                 200                 205
Ile Arg Gly Lys Arg Asp Gly Val Leu Leu Asn Ser Ile Thr Asn Glu
210                 215                 220
Thr Arg Ile Asn Glu Ile Thr Tyr Phe Ser Asp Ala Gln Ala Asn Asp
225                 230                 235                 240
Phe Trp Arg Gly Tyr Thr Asp His Met Val Glu Asn Arg Leu Ile Ser
                245                 250                 255
Thr Thr His Thr Glu His Ile Pro Thr Ile Asn Leu Glu Lys Cys Gly
            260                 265                 270
Lys Arg Met Ala Leu Leu Glu Ile Leu Phe His Ser Thr Phe Lys Ile
        275                 280                 285
Thr Cys Lys His Cys Asn Asn Asp Asp Leu Glu Leu Ser Asp Asp Glu
290                 295                 300
Phe Gly Glu Arg Leu Tyr Lys Asn Leu Ile Arg Ile Glu Glu Lys Gln
305                 310                 315                 320
Lys Glu Tyr Leu Ala Glu Asp Gln Lys Leu Lys Arg Met Ile Ser Phe
                325                 330                 335
Leu Lys Asp Arg Cys Asn Pro Lys Phe Glu His Leu Pro Leu Leu Trp
            340                 345                 350
Gln Val Ala Glu Thr Ile Gly His Tyr Thr Asp Asn Gln Ala Lys Gln
        355                 360                 365
Ile Leu Glu Val Asn Glu Ala Leu Ile Lys Val Asn Thr Leu Ser Val
370                 375                 380
Glu Asp Ala Val Lys Ala Ser Ala Ser Leu Leu Glu Ile Ser Arg Trp
385                 390                 395                 400
Tyr Lys Asn Arg Lys Glu Ser Ser Lys Glu Gly Thr Leu Ser Thr Phe
```

```
                    405                 410                 415
Arg Asn Lys Ile Ser Pro Lys Ser Thr Ile Asn Thr Ala Leu Met Cys
            420                 425                 430

Asp Asn Gln Leu Asp Thr Asn Gly Asn Phe Leu Trp Gly Lys Arg Glu
            435                 440                 445

Tyr His Ala Lys Arg Phe Phe Thr Asn Tyr Phe Glu Ala Val Asp Pro
        450                 455                 460

Lys Asp Thr Tyr Glu Lys His Val Thr Arg Phe Asn Pro Asn Gly Gln
465                 470                 475                 480

Arg Lys Leu Ser Ile Gly Lys Leu Val Ile Pro Leu Asp Phe Gln Lys
                485                 490                 495

Ile Arg Glu Ser Phe Ile Gly Val Gln Val Gln Lys Gln Ala Ile Ser
            500                 505                 510

Arg Ala Cys Leu Ser Lys Ile Glu Asn Asn Tyr Ile Tyr Pro Cys Cys
            515                 520                 525

Cys Val Thr Thr Glu Phe Gly Gln Pro Val Tyr Ser Glu Ile Ile Pro
        530                 535                 540

Pro Thr Lys Gly His Ile Thr Ile Gly Asn Ser Thr Asp Pro Lys Ile
545                 550                 555                 560

Val Asp Leu Pro Asn Ser Asp Pro Pro Met Met Tyr Ile Ala Lys Asp
                565                 570                 575

Gly Tyr Cys Tyr Leu Asn Ile Phe Leu Ala Ala Leu Ile Asn Val Asn
            580                 585                 590

Glu Asp Ser Ala Lys Asp Tyr Thr Lys Phe Leu Arg Asp Glu Leu Ile
            595                 600                 605

Glu Arg Leu Gly Lys Trp Pro Lys Leu Lys Asp Val Ala Thr Ala Cys
        610                 615                 620

Tyr Ala Leu Ser Val Met Phe Pro Glu Ile Lys Asn Ala Glu Leu Pro
625                 630                 635                 640

Gln Ile Leu Val Asp His Glu His Lys Thr Met His Val Ile Asp Ser
                645                 650                 655

Tyr Gly Ser Leu Ser Val Gly Phe His Ile Leu Lys Ala Asn Thr Ile
            660                 665                 670

Gly Gln Leu Ile Lys Met Gln Tyr Glu Ser Met Glu Ser Glu Met Arg
            675                 680                 685

Glu Tyr Val Val Gly Glx
        690

<210> SEQ ID NO 3
<211> LENGTH: 937
<212> TYPE: DNA
<213> ORGANISM: Saccharum hybrid cultivar CP72-1210

<400> SEQUENCE: 3
ggccattatg gccggggaga acactgtatg aagaacatgg ccgcttctta tagtcaagac     60
gcgcagctcg atctcgtact tcctgacgct cccgtcgatg ctagcgcgtc tcgttctgaa    120
cattcatctc agcttgctag ctctaactgg agatctgtga ttcaaaactc cccacctgat    180
ctcctatgcg gatgcggtag accggcaatt aggcgcacgg cagagactgc gaagaacaat    240
ggccgcatct ttcgcacgtg tccggcgtgc aaaatatgga tttggcagga tctgctggac    300
agctatgtga atgctttgat aagctactgt cgtgatgcct ccattgattc ccttcagtca    360
gagcttgaat ctagccgttt attaatttcc gagaagcagg cacagatttc acgtttggag    420
aaacaattgg agacgctgca gccacttatc tcaaaatata ctgaacaatc tcgcagcatt    480
```

```
gctcaggcct ccattccatc atcactttt ttcttggaag cctgcagtct ccgacatcag        540
cggcggaggg tgaatgaaaa tcaaggaggg gctaatttca aaagaagcta ctggagcgat        600
taaagcttcg gttaaaaata agcaagaatc taacacccag agcacaaatt ccatgagctg        660 gcttttttt gggacaccct ttcattttc atcaaaaaag ggggggcacc cccagtttcc        720 tccaaaggc tcccctgtc cgacatcata ggtgatgtga ttacccaaaa acaggttgtc        780
ccgcttgctg actcgatgcc aaatttggat tcaatgctgc tcctgttgtt ttaacaatca        840
atcattttga ctaaaagcat tccccttaaa attgttgtta aatttattgt caaacttatt        900
accgcaaagt ccgttggcag gtaatccccc ccttttt                                 937

<210> SEQ ID NO 4
<211> LENGTH: 200
<212> TYPE: PRT
<213> ORGANISM: Saccharum hybrid cultivar CP72-1210

<400> SEQUENCE: 4

Gly His Tyr Gly Arg Gly Glu His Cys Met Lys Asn Met Ala Ala Ser
1               5                   10                  15

Tyr Ser Gln Asp Ala Gln Leu Asp Leu Val Leu Pro Asp Ala Pro Val
            20                  25                  30

Asp Ala Ser Ala Ser Arg Ser Glu His Ser Ser Gln Leu Ala Ser Ser
        35                  40                  45

Asn Trp Arg Ser Val Ile Gln Asn Ser Pro Pro Asp Leu Leu Cys Gly
    50                  55                  60

Cys Gly Arg Pro Ala Ile Arg Arg Thr Ala Glu Thr Ala Lys Asn Asn
65                  70                  75                  80

Gly Arg Ile Phe Arg Thr Cys Pro Ala Cys Lys Ile Trp Ile Trp Gln
                85                  90                  95

Asp Leu Leu Asp Ser Tyr Val Asn Ala Leu Ile Ser Tyr Cys Arg Asp
            100                 105                 110

Ala Ser Ile Asp Ser Leu Gln Ser Glu Leu Glu Ser Ser Arg Leu Leu
        115                 120                 125

Ile Ser Glu Lys Gln Ala Gln Ile Ser Arg Leu Glu Lys Gln Leu Glu
    130                 135                 140

Thr Leu Gln Pro Leu Ile Ser Lys Tyr Thr Gln Ser Arg Ser Ile
145                 150                 155                 160

Ala Gln Ala Ser Ile Pro Ser Ser Leu Phe Phe Leu Glu Ala Cys Ser
                165                 170                 175

Leu Arg His Gln Arg Arg Val Asn Glu Asn Gln Gly Gly Ala Asn
            180                 185                 190

Phe Lys Arg Ser Tyr Trp Ser Asp
        195                 200

<210> SEQ ID NO 5
<211> LENGTH: 449
<212> TYPE: DNA
<213> ORGANISM: Saccharum hybrid cultivar CP72-1210

<400> SEQUENCE: 5
gaattcggcc attatggccg ggcatgtgc agtgaatgcg ccaaggtcct gaggtaccaa         60
accactcggt gccccatctg caggcagcct gttgagcgtc tcctcgagat caaagtgagc        120
aacaaatctg aagagcagca gcagacgccc aatcgccgc cgctcccagc ccagctctg         180 cagcaggaag aggtgtagcc gtgattaaag tcagttctga gacattatat ggaactagtt        240
```

```
tgcggccttc aggcctttcc ctaaaggttt gttctctcat ctgagcaacg gggaatgtaa      300
ccggtacttt acctttagcc tatgtaagct tctggcatcg catggctttg ccgacctctg      360
ctgtacctgc ttatctggag gtcggagacc aagatgccaa ggaaagtgtg taccgtatat      420
taaaaaaaaa aaaaaaaaaa aaaaaaaaa                                        449
```

<210> SEQ ID NO 6
<211> LENGTH: 149
<212> TYPE: PRT
<213> ORGANISM: Saccharum hybrid cultivar CP72-1210

<400> SEQUENCE: 6

```
Glu Phe Gly His Tyr Gly Arg Gly Met Cys Ser Glu Cys Ala Lys Val
1               5                   10                  15

Leu Arg Tyr Gln Thr Thr Arg Cys Pro Ile Cys Arg Gln Pro Val Glu
            20                  25                  30

Arg Leu Leu Glu Ile Lys Val Ser Asn Lys Ser Glu Gln Gln Gln
        35                  40                  45

Thr Pro Gln Ser Pro Pro Leu Pro Ala Pro Ala Leu Gln Gln Glu Glu
    50                  55                  60

Val Glx Pro Glx Leu Lys Ser Val Leu Arg His Tyr Met Glu Leu Val
65                  70                  75                  80

Cys Gly Leu Gln Ala Phe Pro Glx Arg Phe Val Leu Ser Ser Glu Gln
                85                  90                  95

Arg Gly Met Glx Pro Val Leu Tyr Leu Glx Pro Met Glx Ala Ser Gly
            100                 105                 110

Ile Ala Trp Leu Cys Arg Pro Leu Leu Tyr Leu Leu Ile Trp Arg Ser
        115                 120                 125

Glu Thr Lys Met Pro Arg Lys Val Cys Thr Val Tyr Glx Lys Lys Lys
    130                 135                 140

Lys Lys Lys Lys Lys
145
```

<210> SEQ ID NO 7
<211> LENGTH: 872
<212> TYPE: DNA
<213> ORGANISM: Saccharum hybrid cultivar CP72-1210

<400> SEQUENCE: 7

```
gaattcggcc attatggccg ggaccaggaa ctccaggaat cagatgacaa ctcggggtat       60
agagctcctg aagtgaccat gtccggtcag tattctcaaa agagtgatgt ttacagcttt      120
ggtgtcgtca tgcttgagct actgactgga cagaaagcat tgacagctc tcgggcaagg      180 tcccagcaat cactagtccg gtgggcttca ccgcagctgc acgacatcga ctcgctagat      240
cagatggttg atccaacctt agaggggctg taccatgcga atcactctc tcggttcgca      300 gacgcaatcg ctctctgtgt ccagcctgaa ccagaattca ggccaccaat gtcggaggtc      360
gtccagtcac tggtccgtct tgtgcagcga gcaagcatgg ggacagcact aagcagcgag      420
tggaattctt gccagttcga tgaatctggt gatcacacgc tctagggaaa atgatgtgt       480 atttcctaga gagtctgatg aggaactata gaaggctcac aagtcataga acttgcagc      540 ttggcattgt tgtgagttgt gacggtgtga catgtgccag tgtcaggtga atgtgactt      600 ttacctatgc cattttactg agagtctgct gcaacctgaa gtaggggtga aaagaaagtt      660
ccttctttaa aaatatatat ggttcattcg gacgtgtata tgaatatctt ttgaagacaa      720
```

```
tcaactttct gatttcgtct ctgatcgctg tccaaaaatt atcagggaag atgtagcact   780
agtcctgcca cagaattagt catctgtata tcctcagaaa tccgaaccat atccaggaaa   840
catcaacaga ggacacgtcc acatattcga ac                                 872
```

<210> SEQ ID NO 8
<211> LENGTH: 290
<212> TYPE: PRT
<213> ORGANISM: Saccharum hybrid cultivar CP72-1210

<400> SEQUENCE: 8

```
Glu Phe Gly His Tyr Gly Arg Asp Gln Glu Leu Gln Glu Ser Asp Asp
 1               5                  10                  15

Asn Ser Gly Tyr Arg Ala Pro Glu Val Thr Met Ser Gly Gln Tyr Ser
            20                  25                  30

Gln Lys Ser Asp Val Tyr Ser Phe Gly Val Val Met Leu Glu Leu Leu
        35                  40                  45

Thr Gly Gln Lys Ala Phe Asp Ser Ser Arg Ala Arg Ser Gln Gln Ser
    50                  55                  60

Leu Val Arg Trp Ala Ser Pro Gln Leu His Asp Ile Asp Ser Leu Asp
65                  70                  75                  80

Gln Met Val Asp Pro Thr Leu Glu Gly Leu Tyr His Ala Lys Ser Leu
                85                  90                  95

Ser Arg Phe Ala Asp Ala Ile Ala Leu Cys Val Gln Pro Glu Pro Glu
            100                 105                 110

Phe Arg Pro Pro Met Ser Glu Val Val Gln Ser Leu Val Arg Leu Val
        115                 120                 125

Gln Arg Ala Ser Met Gly Thr Ala Leu Ser Ser Glu Trp Asn Ser Cys
    130                 135                 140

Gln Phe Asp Glu Ser Gly Asp His Thr Leu Glx Gly Lys Met Met Cys
145                 150                 155                 160

Ile Ser Glx Arg Val Glx Glx Gly Thr Ile Glu Gly Ser Gln Val Ile
                165                 170                 175

Glu Thr Cys Ser Leu Ala Leu Leu Glx Val Val Thr Val Glx His Val
            180                 185                 190

Pro Val Ser Gly Glu Met Glx Leu Leu Pro Met Pro Phe Tyr Glx Glu
        195                 200                 205

Ser Ala Ala Thr Glx Ser Arg Gly Glu Lys Lys Val Pro Ser Leu Lys
    210                 215                 220

Ile Tyr Met Val His Ser Asp Val Tyr Met Asn Ile Phe Glx Arg Gln
225                 230                 235                 240

Ser Thr Phe Glx Phe Arg Leu Glx Ser Leu Ser Lys Asn Tyr Gln Gly
                245                 250                 255

Arg Cys Ser Thr Ser Pro Ala Thr Glu Leu Val Ile Cys Ile Ser Ser
            260                 265                 270

Glu Ile Arg Thr Ile Ser Arg Lys His Gln Gln Arg Thr Arg Pro His
        275                 280                 285

Ile Arg
    290
```

<210> SEQ ID NO 9
<211> LENGTH: 1141
<212> TYPE: DNA
<213> ORGANISM: Saccharum hybrid cultivar CP72-1210

<400> SEQUENCE: 9

-continued

```
gaattcggcc attatggccg gggaccgcag ttcccccgac cacaccgttc cgccgcgcac        60
agaggccagc cccgcgccag gagtaagttt gttcttttta acaatatgtc gagggaggag       120
aatgtttaca tggccaagct ggctgagcag gccgaaaggt atgaggagat ggttgagtat       180
atggagaagg tggctaagac tgtagatgtt gaagagctca ctgtggagga gcgtaacctc       240
ctgtctgtcg catacaagaa tgtgattggg gctcgccgtg cttcatggcg cattgtctct       300
tccattgaac agaaggagga gtcccgtaag aacgaagagc atgtgaacct tatcaaggaa       360
taccgcggga agattgaggc tgaactgagc aacatctgtg atggcatcct gaaactgctt       420
gactcccacc tagtgccttc ctctactgct gctgaatcaa aggtcttcta cctcaagatg       480
aagggtgact atcacaggta tcttgcggaa tttaagactg gtgctgagag gaaggaatct       540
gctgagagca caatggtagc ctacaaggct gctcaggaca ttgctctggc tgagctggca       600
cctacacatc cgataaggct tgggcttgct cttaacttct cagtgttcta ttatgagatt       660
ctgaactccc cagacaaagc ttgcaacctt gcaaagcagg cgtttgatga agctatctct       720
gagttagaca cccttgggga ggagtcatac aaagatagca ctctgatcat gcagctcctg       780
agggacaact tgacccttttg gacctctgac ctcacggagg atggtgctga tgagggcaaa       840
gaagcctcaa aaggtgatgc tggcgaggga cagtaatctt cggagagggc atgttgttcc       900
agcctggttt tagatgctct atgctgtcga agctgtgccg tgccattatt gtagcagatt       960
tcctctcccc ctcacttcat ttgcctcata ttagtaggct ggtagtggtc gaattagttc      1020
ccattgcttt gtgttgcagc tagttggcac taggtccgtg tggactggta ttgttccccct     1080 ggatttgaca agcatgtcct gtggtcgctc tagcgtttta ttgagctttg aagcctcgat      1140
t                                                                     1141
```

<210> SEQ ID NO 10
<211> LENGTH: 380
<212> TYPE: PRT
<213> ORGANISM: Saccharum hybrid cultivar CP72-1210

<400> SEQUENCE: 10

```
Glu Phe Gly His Tyr Gly Arg Gly Pro Gln Phe Pro Arg Pro His Arg
1               5                   10                  15

Ser Ala Ala His Arg Gly Gln Pro Arg Ala Arg Ser Lys Phe Val Leu
            20                  25                  30

Phe Asn Asn Met Ser Arg Glu Glu Asn Val Tyr Met Ala Lys Leu Ala
        35                  40                  45

Glu Gln Ala Glu Arg Tyr Glu Glu Met Val Glu Tyr Met Glu Lys Val
    50                  55                  60

Ala Lys Thr Val Asp Val Glu Glu Leu Thr Val Glu Glu Arg Asn Leu
65                  70                  75                  80

Leu Ser Val Ala Tyr Lys Asn Val Ile Gly Ala Arg Arg Ala Ser Trp
                85                  90                  95

Arg Ile Val Ser Ser Ile Glu Gln Lys Glu Glu Ser Arg Lys Asn Glu
            100                 105                 110

Glu His Val Asn Leu Ile Lys Glu Tyr Arg Gly Lys Ile Glu Ala Glu
        115                 120                 125

Leu Ser Asn Ile Cys Asp Gly Ile Leu Lys Leu Leu Asp Ser His Leu
    130                 135                 140

Val Pro Ser Ser Thr Ala Ala Glu Ser Lys Val Phe Tyr Leu Lys Met
145                 150                 155                 160

Lys Gly Asp Tyr His Arg Tyr Leu Ala Glu Phe Lys Thr Gly Ala Glu
```

```
                165                 170                 175
Arg Lys Glu Ser Ala Glu Ser Thr Met Val Ala Tyr Lys Ala Ala Gln
                180                 185                 190

Asp Ile Ala Leu Ala Glu Leu Ala Pro Thr His Pro Ile Arg Leu Gly
            195                 200                 205

Leu Ala Leu Asn Phe Ser Val Phe Tyr Tyr Glu Ile Leu Asn Ser Pro
        210                 215                 220

Asp Lys Ala Cys Asn Leu Ala Lys Gln Ala Phe Asp Glu Ala Ile Ser
225                 230                 235                 240

Glu Leu Asp Thr Leu Gly Glu Glu Ser Tyr Lys Asp Ser Thr Leu Ile
                245                 250                 255

Met Gln Leu Leu Arg Asp Asn Leu Thr Leu Trp Thr Ser Asp Leu Thr
                260                 265                 270

Glu Asp Gly Ala Asp Glu Gly Lys Glu Ala Ser Lys Gly Asp Ala Gly
            275                 280                 285

Glu Gly Gln Glx Ser Ser Glu Arg Ala Cys Cys Ser Ser Leu Val Leu
        290                 295                 300

Asp Ala Leu Cys Cys Arg Ser Cys Ala Val Pro Leu Leu Glx Gln Ile
305                 310                 315                 320

Ser Ser Pro Pro His Phe Ile Cys Leu Ile Leu Val Gly Trp Glx Trp
                325                 330                 335

Ser Asn Glx Phe Pro Leu Leu Cys Val Ala Ala Ser Trp His Glx Val
                340                 345                 350

Arg Val Asp Trp Tyr Cys Ser Pro Gly Phe Asp Lys His Val Leu Trp
            355                 360                 365

Ser Leu Glx Arg Phe Ile Glu Leu Glx Ser Leu Asp
        370                 375                 380

<210> SEQ ID NO 11
<211> LENGTH: 829
<212> TYPE: DNA
<213> ORGANISM: Saccharum hybrid cultivar CP72-1210

<400> SEQUENCE: 11
gaattcggcc attatggccg ggctgttcaa gctggaccgt tatatggtat gggacaccat    60
ggatcttcca ccacaattgc ttatggcggt gcatacttgc catattcttc ctcaactgga   120
caatcgagca ataatcatca gagcatgga tttcctgagc ggccagggca gcctgagtgt   180
caatatttta tgaggactgg aggttgcaaa tttggaacta tgtgtaaata taaccatcct   240
cgagattgga gcactcctaa gtccaactac atgttcagtc atctctgcct tccacttcgt   300
ccgggtgctc agccttgtgc gtactatgca caaaatggat attgcagata tggagttgca   360
tgcaaatatg atcacccaat gggtacacta ggctacagtt catctgcttt accctatct   420
gacatgccaa ttgctcccta ccctatcggc ttctctgttg ccacgttggc tccatcttca   480
tcttccccag aatatatttc aaccaaagat ccatcaatca ccaagtagc atcaccagtg   540
cagcacccga acatgttgga acaatcttgc caaaagggt ttcccttcgg atccattatg   600
cgaactcaac ttctacaagt gtcggcagtt caagcctggg gggcgctgat tttctgactg   660
ggggatgatc cttaacacaa atttctatac ttgaacagtt tgaagccttc aaggaataaa   720
aactggggcc ttgaaaaacc gggaggggtt cttcccaaat aaaactgtgg tcaacactca   780
tcctgaattg gtttcctatt caaacggaag aggtttagga gtcacattg               829

<210> SEQ ID NO 12
```

-continued

```
<211> LENGTH: 276
<212> TYPE: PRT
<213> ORGANISM: Saccharum hybrid cultivar CP72-1210

<400> SEQUENCE: 12

Glu Phe Gly His Tyr Gly Arg Ala Val Gln Ala Gly Pro Leu Tyr Gly
 1               5                  10                  15

Met Gly His His Gly Ser Ser Thr Thr Ile Ala Tyr Gly Gly Ala Tyr
                20                  25                  30

Leu Pro Tyr Ser Ser Ser Thr Gly Gln Ser Ser Asn Asn His Gln Glu
            35                  40                  45

His Gly Phe Pro Glu Arg Pro Gly Gln Pro Glu Cys Gln Tyr Phe Met
        50                  55                  60

Arg Thr Gly Gly Cys Lys Phe Gly Thr Met Cys Lys Tyr Asn His Pro
 65                 70                  75                  80

Arg Asp Trp Ser Thr Pro Lys Ser Asn Tyr Met Phe Ser His Leu Cys
                85                  90                  95

Leu Pro Leu Arg Pro Gly Ala Gln Pro Cys Ala Tyr Tyr Ala Gln Asn
            100                 105                 110

Gly Tyr Cys Arg Tyr Gly Val Ala Cys Lys Tyr Asp His Pro Met Gly
        115                 120                 125

Thr Leu Gly Tyr Ser Ser Ser Ala Leu Pro Leu Ser Asp Met Pro Ile
130                 135                 140

Ala Pro Tyr Pro Ile Gly Phe Ser Val Ala Thr Leu Ala Pro Ser Ser
145                 150                 155                 160

Ser Ser Pro Glu Tyr Ile Ser Thr Lys Asp Pro Ser Ile Asn Gln Val
                165                 170                 175

Ala Ser Pro Val Gln His Pro Asn Met Leu Glu Gln Ser Cys Gln Lys
            180                 185                 190

Gly Phe Pro Phe Gly Ser Ile Met Arg Thr Gln Leu Leu Gln Val Ser
        195                 200                 205

Ala Val Gln Ala Trp Gly Ala Leu Ile Phe Glx Leu Gly Asp Asp Pro
210                 215                 220

Glx His Lys Phe Leu Tyr Leu Asn Ser Leu Lys Pro Ser Arg Asn Lys
225                 230                 235                 240

Asn Trp Gly Leu Glu Lys Pro Gly Gly Val Leu Pro Lys Glx Asn Cys
                245                 250                 255

Gly Gln His Ser Ser Glx Ile Gly Phe Leu Phe Lys Arg Lys Arg Phe
            260                 265                 270

Arg Ser His Ile
            275
```

ISOLATION OF PROTEINS INVOLVED IN POSTTRANSCRIPTIONAL GENE SILENCING AND METHODS OF USE

The present application claims priority to U.S. Provisional Patent Application Ser. No. 60/314,863 filed on Aug. 24, 2001 and incorporated by reference herein.

TECHNICAL FIELD OF THE INVENTION

The present invention relates generally to sugarcane protein isolation and more particularly to isolation and characterization of proteins that are involved in posttranscriptional gene silencing. The invention also includes sugarcane and sorghum mosaic virus proteins involved in silencing and the cDNAs which encode them. Finally the invention includes use of these cDNAs and proteins to regulate silencing.

BACKGROUND OF THE INVENTION

In the course of evolution organisms have developed a spectrum of defense mechanisms that target alien, parasitic elements. The most specialized defense system is perhaps the vertebrate immune system, which provides effective protection against a wide range of infectious microbes. In the vertebrate immune system, it is essentially peptides that are recognized as non-self and eliminated. Transgenic plant studies have revealed the existence of another, more ancestral level of defense response. Homology-dependent gene silencing can be viewed as a novel, innate host defense system that is capable of recognizing foreign nucleic acids as non-self and inactivating or removing them from the cell. First recognized in plants and fungi, homology-dependent gene silencing mechanisms have now been shown to operate in a wide range of eukaryotic organisms. In plants, this type of gene silencing may occur at the level of DNA, by inhibition of transcription, or at the level of RNA, by enhanced RNA turnover. Both viral RNA and transgenes are subject to these host surveillance systems, which are only poorly understood at the molecular level. At the core of both silencing events resides a molecular mechanism that is able to recognize nucleic acid sequence homology.

Transgene-induced gene silencing in plants was originally described as the coordinated suppression of transgenes that share sequence similarity (Depicker and Van Montagu, 1997). This phenomenon is most often induced when multiple copies of a transgene are present at a single locus. Silencing not only affects all genes in that locus, i.e. in cis, but also acts in trans, and additionally down-regulates the expression of other, unlinked transgene(s). Silencing can also affect the expression of endogenous genes, provided they have sequence similarity to the silencing transgene, a phenomenon referred to as cosuppression (Napoli et al., 1990; Van der Krol et al., 1990).

In plants, cases of transgene-induced gene silencing belong to two different mechanistic classes: those that occur at the level of transcription and those that are due to enhanced RNA turnover. Transcriptional gene silencing (TGS) requires sequence identity in the promoter region and is associated with methylation and inactivation of the promoter sequences of the affected genes (Kumpatla et al., 1998). In posttranscriptional gene silencing (PTGS), the (trans)genes remain actively transcribed but the steady-state RNA levels are highly reduced due to sequence-specific RNA degradation. Some instances of PTGS are associated with DNA methylation located in the transcribed portion of the genes (Ingelbrecht et al., 1994; 1999).

The expression level, number and configuration of the integrated transgenes as well as developmental and environmental factors can all influence the occurrence of transgene-induced gene silencing. Importantly, transgene-induced gene silencing in plants is reversible, and in the absence of the silencer locus, expression of endogenous genes or other transgenes can be restored to normal. The changes in gene expression are therefore not due to irreversible changes in DNA but rather are epigenetic.

PTGS behaves as a non-clonal event and, in agreement with this, it has been shown that a sequence-specific signal is involved in the systemic spread of PTGS (Palauqui et al., 1997; Voinnet and Baulcombe, 1997). These experiments allow differentiation of separate initiation and maintenance phases in PTGS and further suggest that a molecular system amplifies the silencing signal during the course of long-distance movement of PTGS. Mutants that enhance (Dehio and Schell, 1994) or suppress (Elmayan et al., 1998; Mourrain et al., 2000; Dalmay et al, 2000) PTGS have been isolated in *Arabidopsis thaliana* but only two of the corresponding genes have been cloned (Mourrain et al., 2000; Dalmay et al, 2000). One of these has no significant similarity with any known or putative protein (Mourrain et al., 2000) and the other is similar to a RNA-dependent RNA polymerase (RdRp; Mourrain et al., 2000; Dalmay et al, 2000). Establishment of PTGS in plants requires separately identifiable initiation, spread, and maintenance phases, but the proteins involved in these pathways have not been characterized.

Plant virus studies have greatly contributed to the current understanding of gene silencing in general and PTGS in particular. Applying the concept of pathogen-derived resistance, viral genes were introduced into plants and resulted in virus resistant phenotypes. Many resistance phenotypes do not require the expression of a functional protein but are mediated at the level of RNA. It is now an established fact that a mechanism similar to PTGS is the underlying molecular mechanism in most of these cases (van den Boogaart et al., 1998).

Posttranscriptional silencing of an endogenous plant gene or transgene can be triggered by replication of a recombinant virus that carries sequences homologous to these genes (Kumagai et al., 1995; Ruiz et al., 1998). This process involves sequence-specific RNA turnover, similar to PTGS induced by transgenes, hence the term virus-induced gene silencing. Moreover, natural virus infection of non-transgenic plants can induce a resistance mechanism that is strain-specific and targeted against RNA, similar to RNA-mediated resistance induced by (silenced) transgenes (Ratcliff et al., 1997; Covey et al., 1997). Transgene- and virus-induced gene silencing are collectively described as homology-dependent gene silencing because these mechanisms all target homologous nucleic acid sequences. It was proposed that homology-dependent gene silencing acts as a natural plant defense mechanism against invading DNA or RNA elements (Matzke and Matzke, 1998).

The demonstration that plant viral proteins can suppress PTGS provides direct evidence that PTGS functions as a host defense response in plants (Anandalakshmi et al., 1998; Brigneti et al., 1998; Kasschau and Carrington, 1998). At least 5 different proteins encoded by unrelated DNA and RNA viruses of plants have now been shown to act as suppressors of PTGS in *Nicotiana benthamiana*. Importantly, the suppression phenotypes induced by these viral proteins are distinct indicating that separate steps of the host PTGS defense system are targeted. For example, the potyviral helper-component proteinase (HC-Pro) can reverse the effects of PTGS in tissues that were previously silenced, whereas the 2b protein of Cucumber mosaic virus only affects initiation of PTGS (Voinnet et al., 1999). Although potyviral HC-Pro by itself is sufficient to suppress transgene-induced silencing, it appears that the potyviral P1 protein can enhance its ability to suppress virus-induced gene silencing (Anandalakshmi et al., 1998; V. Vance). The discovery of viral suppressors of silencing phenomena is unique to plants. So far, no animal or fungal viruses have been shown to suppress PTGS in these organisms.

It has been proposed that 'aberrant' RNA molecules trigger PTGS in plants (Lindbo et al., 1993). The exact nature of this aberrant RNA is unknown but it could be double-stranded RNA (dsRNA) (Waterhouse et al., 1998), prematurely terminated transcripts, levels of RNA that exceed a certain threshold, or some other unusual characteristic. These RNA molecules would serve as templates for an RNA-dependent RNA polymerase (RdRp) and lead to the production of short complementary RNAs (cRNA). These cRNAs would then anneal with homologous mRNAs or viral RNAs and the resulting double-stranded RNA would be degraded by double strand-specific RNases. This model accounts for the sequence-specific RNA turnover and several aspects of it are supported by experimental data. For example, an RdRp that is induced during viral infection has been cloned in tomato (Schiebel et al., 1998) and small cRNAs have recently been identified in transgenic plants that display PTGS (Hamilton and Baulcombe, 1999). The identification of a double strand-specific RNase in *Caenorhabditis elegans* and a RdRp-like protein in *Neurospora crassa,* and recently in *Arabadopsis*, as essential components of PTGS-like mechanisms in these organisms (see below) provides further support for this hypothesis.

RNA-mediated genetic interference (RNAi) in *C. elegans* is a process that closely resembles PTGS in plants: both act at the posttranscriptional level and result in sequence-specific RNA turnover (Tabara et al., 1998; Montgomery and Fire, 1998). The trigger for RNAi in *C. elegans* is well characterized and consists of dsRNA (Sharp, 1999). RNA-specific silencing can be induced by locally injecting homologous dsRNA molecules in a few cells. Silencing then spreads from the site of injection into neighboring cells and tissues and is even transmitted to the F1 progeny. The ability of silencing to move both in space and over time strongly suggests that amplification of the silencing signal is taking place, similar to PTGS in plants.

Recently, several genes have been identified in *C. elegans* that are required for this interference process. The MUT-7 gene encodes a homolog of RNaseD, which is a double strand-specific RNase (Ketting et al., 1999). The RDE-1 gene belongs to a family of genes that are conserved from plants to vertebrates and several members of this family are required for gene silencing mechanisms in animal systems (Tabara et al., 1999). Interestingly, mutations in both these genes reactivate mobilization of endogenous transposons, suggesting that one function of RNAi is transposon silencing. Sequence-specific inhibition of gene function by dsRNA has also been demonstrated in *trypanosomes, Drosophila* and *planaria* and has been used in these organisms as a method to determine gene functions (Kennerdell and Carthew, 1998; Misquitta and Patterson, 1999; Sanchez Alvarado and Newmark, 1999).

Transgene-induced PTGS is termed 'quelling' in the fungus *N. crassa* (Cogoni and Macino, 1997a). Quelling-defective (qde) mutants of *N. crassa,* in which transgene-induced gene silencing is impaired, have been isolated and could be classified in three qde complementation groups (Cogoni and Macino, 1997b). Two QDE genes that belong to two different complementation groups, have recently been cloned. The QDE-1 gene encodes a protein that contains an RdRp-motif (Cogoni and Macino, 1999a) and QDE-3 belongs to the RecQ DNA helicase family (Cogoni and Macino, 1999b).

As summarized above, there has been substantial progress in the general understanding of PTGS in plants and its importance as part of a general defense system is now fully appreciated. However, all of the biochemical pathways of PTGS and the enzymes that are involved have not yet been elucidated in plants. Insight into these mechanisms may come from analyzing mutants that are defective in PTGS. This approach has already been used with success in *Neurospora* and *C. elegans* and is currently also being followed for *Arabidopsis*. While this strategy is relatively straightforward and will surely result in the identification of genes that play a central role in this process, there are also limitations. For example, gene redundancies and possibly lethal, loss-of-function phenotypes might prevent identification of certain genes. There are also practical problems in generating and screening a sufficiently large number of mutants which limit this approach to model plants such as *Arabidopsis.*

An alternative or complementary approach involves directly identifying the host factors that mediate PTGS. The identification of viral proteins as suppressors of PTGS provides the necessary tools to pursue this strategy.

Identification and characterization of proteins that interact with a viral suppressor of PTGS will have an impact on understanding fundamentals of virus-host plant interactions, particularly on the mechanisms that plants employ to combat viral infection and on the counterdefensive strategies that viruses use to suppress or evade these responses. To date, viral suppression of PTGS is a process unique to plants. However, because PTGS is a defense mechanism that is conserved among various eukaryotic kingdoms, the identified protein interactions might also shed light on the molecular mechanisms of silencing phenomena in other organisms.

In addition to significance for basic (plant) molecular virology, establishing the biochemical pathways of host defense responses will facilitate the development of improved virus control strategies in plants. PTGS-based approaches for virus control are already in use but the lack of a solid understanding of the phenomenon necessitates a more empirical approach and has an uncertain outcome. Also, such approaches are currently limited because of their narrow range. Possible and realistic improvements involve enhanced and more predictable triggering and broadening the scope of the PTGS defense system.

Use of the method of the present invention will also contribute to plant genetic engineering in general. It is now clear that transgenes in plants (and other organisms) can be perceived as intrusive elements and consequently are inactivated. Developing procedures that allow stable and predictable transgene expression is one of the challenges of genetic engineering. The monocot crop plants provide the most important source of food worldwide and offer great potential for improvement through genetic transformation, not only for traits related to food production but also as recombinant expression systems for high value products.

Finally, gene silencing can be used as a way to produce 'knock-out' phenotypes in reverse genetic studies. This has already been successfully applied in animal systems and its potential has been demonstrated in plants. With an increasing number of genes being discovered in sugarcane, many of which have no known function, it can be expected that these approaches will become even more important in the future.

Thus, the yeast two-hybrid method of the present invention has been used to unravel the pathway(s) of PTGS and plant defense responses and novel, key proteins involved in this process have been identified. In doing so, a cDNA library from silenced plant tissues rather than non-silence plant tissues has been used. These proteins and genes can be applied towards regulating PTGS of transgenes, endogenous plant genes, and viral genes. Specific applications of the present invention include but are not limited to, improved strategies for engineered virus resistance, increased expression of transgenes by inhibiting silencing, and modulation of silencing of native genes to obtain desirable traits or in functional genomic studies.

SUMMARY OF THE INVENTION

The present invention includes a method of isolating nucleic acid encoding a plant polypeptide active in PTGS. As used throughout the application, plant may mean a mature plant, an embryonic callus, or other stages of plant development. It may also mean a portion of a plant, a plant tissue, or a plant cell.

The first step of a method of the above method involves selecting a bait nucleic acid which encodes a bait protein active in PTGS in plants or suppressive of PTGS in plants. After bait selection, a cDNA prey library may be prepared from a plant that actively exhibits PTGS at the time of library generation. If an entire plant exhibiting PTGS is not available, tissues in which PTGS is exhibited may be selected.

After the bait and prey are selected, a yeast two-hybrid assay may be conducted with the bait and prey nucleic acids. Prey cDNA that yields a true positive yeast two-hybrid assay result encodes a polypeptide active in PTGS in the plant. True positive status may be verified using methods known in the art, such as null controls, reversal of bait and prey, and in vitro and in planta studies of interactions. Such in vitro assay may include farwestern blot assays and pull down assays. They may be performed under plant physiological conditions to eliminate false negatives and false positives. In planta studies may be performed in an embryonic callus or other plant tissue.

In an exemplary embodiment of the above method of the present invention, the bait nucleic acid comprises a sequence selected from SEQ. ID. NO. 1, SEQ. ID. NO. 3, SEQ. ID. NO. 5, SEQ. ID. NO. 7, SEQ. ID. NO. 9, or SEQ. ID. NO. 11. The entire nucleic acids of these sequences may be used or only portions thereof. Additionally, substituted nucleic acids and nucleic acids with similar identities may also be used.

In another exemplary embodiment the plant is a monocot, particularly sugarcane and more particularly Saccharum hybrid cultivar CP72-1210.

The present invention also includes several SrMV and sugarcane novel proteins and nucleic acids. Novel nucleic acids are provided in SEQ. ID. NOS. 1, 3, 5, 7, 9 and 11. Novel amino acid sequences are provided in SEQ. ID. NOS. 2, 4, 6, 8, 10 and 12. It will be apparent to one skilled in the art that portions of these nucleic acids and proteins or polypeptides may be used in various applications. Additionally, it will be apparent to one skilled in the art that nucleic acids and proteins or polypeptides with high similarity, particularly in regions related to functional domains, may also be substituted. The present invention includes such variations up to the point of disclosures already in the prior art. Each of these proteins is involved in PTGS either as an activator or suppressor. Some proteins may fail to function alone and may rather require or assist another protein for their PTGS-related functions.

The present invention additionally includes transgenic plants including any of the above novel nucleic acids, proteins or polypeptides. In particular, the invention includes a transgenic plant in which PTGS is suppressed that includes the nucleic acid of SEQ. ID. NO. 1 or the protein of SEQ. ID. NO. 2. It also includes a transgenic plant in which PTGS is enhanced that includes the nucleic acid of SEQ. ID. NO. 3 or the protein of SEQ. ID. NO. 4.

The invention additionally includes a method of increasing viral resistance in a plant in which a protein suppressive of PTGS in the plant is selected and the plant is transformed with a nucleic acid encoding the PTGS suppressive protein.

Another method of the invention involves a method of increasing expression of a transgene in a plant by selecting a protein active in PTGS in the plant and transforming the plant with a nucleic acid encoding the protein active in PTGS.

Yet another method of the present invention involves suppressing expression of a native gene in a plant by preparing a vector including a nucleic acid with a sequence of the coding portion of the gene wherein the nucleic acid, upon transcription, products an mRNA molecule double stranded in the region corresponding the to the coding portion of the gene. A plant is then transformed with the vector.

BRIEF DESCRIPTION OF THE DRAWINGS

For a more complete understanding of the present invention and the advantages thereof, reference is now made to the following description taken in conjunction with the accompanying drawings, wherein like reference numbers represent like parts, and which:

FIG. 1A provides the cDNA (SEQ. ID. NO. 1) and FIG. 1B provides the amino acid (SEQ. ID. NO. 2) sequences for Sorghum Mosaic Virus (SrMV) P1/HC-Pro according to an embodiment of the present invention;

FIG. 6A is the cDNA sequence of the RNase H-like protein (SEQ. ID. NO. 3) and FIG. 6B is the encoded amino acid sequence (SEQ. ID. NO. 4), according to an embodiment of the present invention;

FIG. 7A is the cDNA sequence of the sugarcane RING zinc finger protein that interacts with SrMV HC-Pro (SEQ. ID. NO. 5); FIG. 7B is the encoded amino acid sequence (SEQ. ID. NO. 6) according to an embodiment of the present invention;

FIG. 8A is the cDNA sequence of the LRR (leucine-rich repeat) transmembrane protein kinase that interacts with SrMV HC-Pro (SEQ. ID. NO. 7); FIG. 8B is the encoded amino acid sequence (SEQ. ID. NO. 8) according to an embodiment of the present invention;

FIG. 9A is the cDNA sequence of a nucleic acid encoding the sugarcane 14-3-3 protein that interacts with the RNase H-like protein (SEQ. ID. NO. 9); FIG. 9B is the encoded amino acid (SEQ. ID. NO. 10), according to an embodiment of the invention;

FIG. 10A is the cDNA sequence of the sugarcane RING zinc finger protein that interacts with RNase H-like protein (SEQ. ID. NO. 11) and FIG. 10B provides the encoded amino acid sequence (SEQ. ID. NO. 12) according to an embodiment of the present invention;

DETAILED DESCRIPTION OF EXAMPLE EMBODIMENTS OF THE INVENTION

Figure 2:
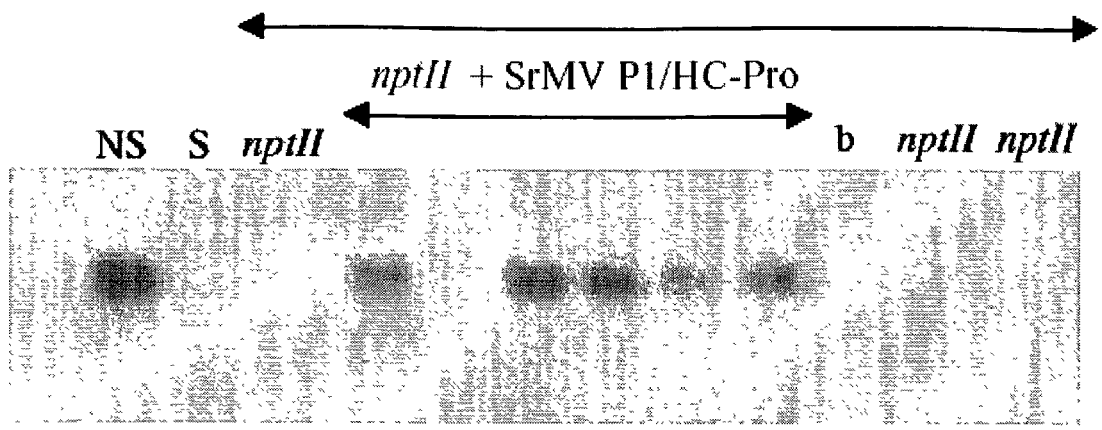
FIG. 2 is a Northern analysis of SrMV (coat protein) CP mRNA in which the lane labeled "S" includes mRNA derived from a plant posttranscriptionally silenced for SrMV CP; lanes labeled "Retransformed S" include mRNA from samples of the silenced plant which were retransformed with either nptII alone or with nptII and SrMV P1/HC-Pro; the lane including mRNA from a plant that is not silenced is labeled "NS"; and the empty lane is labeled "b"

The present invention includes a novel method for determination of plant proteins active in PTGS or suppressive of PTGS. The invention may be used in both monocot and dicot plants, including sugarcane.

The methods of the present invention may be used, inter alia: (i) to identify, isolate and characterize cellular proteins that interact with these PTGS suppressive viral proteins or plant proteins involved in PTGS using a yeast two-hybrid system; and (ii) to evaluate these plant/viral protein interactions in vitro under physiological conditions and in vivo in either transient studies or in transgenic plants, such as sugarcane, expressing these viral proteins. Because many viral proteins such as P1 and HC-Pro are multifunctional proteins involved in various aspects of plant/potyvirus interactions, the methods may also be used to assess the role of interacting host proteins in gene silencing. The methods may be carried out using a combination of molecular genetics, immunological studies, transient antisense suppression studies, and plant transformation.

The overall method includes using a yeast two-hybrid system to search for plant proteins that interact with viral suppressors of PTGS to identify proteins involved in PTGS. These proteins or proteins identified as having a role in PTGS through other methods may then serve as bait to locate other proteins involved in PTGS. Because proteins that interact with other proteins involved in PTGS may be either suppressive of or active in PTGS, the yeast two-hybrid assays may identify both types of proteins. Whether the proteins involved in PTGS are active in or suppressive of PTGS may be determined through a variety of methods, including identification of motifs with particular functions, comparison with known proteins, and in planta studies.

In the present invention the bait protein may be either active in PTGS or may function as a suppressor. The prey used is derived from an expression library of the plant of interest. In an exemplary embodiment of the invention, the prey library is derived from a plant in which PTGS is occurring. This facilitates identification of proteins involved in PTGS because such proteins are actively being produced in the silenced plant and may therefore be better represented in the mRNA pool of a silenced plant than in a non-silenced plant.

After identification of an interacting prey, the bait and prey portions of the two-hybrid screen of the present invention may be reversed to help identify false positives. Comparison with controls designed to look for activation of the reporter system absent either the biat or prey may also be used to identify false positives.

Such yeast two-hybrid screens may then be followed by assays such a farwestern blots or pull down assays to further determine whether identified proteins are false positives and also to characterize their function. In planta physiological conditions may be used in such assays.

In planta studies may also be conducted using transiently or permanently transformed embryonic calli transformed with either a test protein or a DNA encoding a double stranded mRNA of the test protein (which induces PTGS of that protein) in order to further evaluate the suppressive or effective role of the test protein in PTGS.

Proteins identified in one or more of the above screens may also be further characterized by identifying putative functional domains and also be searching for overall cDNA and amino acid sequence similarity with other proteins.

Often proteins and cDNAs identified using the above methodologies may be novel and patentable. In the present invention, five such novel proteins and cDNAs have been identified: the sugarcane 14-3-3 protein and cDNA, the RNase H-like protein and cDNA, the sugarcane LRR transmembrane protein kinase and cDNA, and the two sugarcane RING zinc finger proteins and cDNAs. Additionally, the SrMV P1/HC-Pro protein and cDNA used in some embodiments of the method of the present invention are also novel.

The above cDNAs as well as other identified using the methodologies of the present invention may also be used to construct transgenic plants, plant cells and plant tissues (collectively "plant entities") in which PTGS is either enhanced or suppressed. The methodologies used in the assay methods to generate embryonic calli and other methods know to the art may be used to construct these transgenic plant entities. Transformation may be transient or permanent, depending upon the intended use of the transgenic plant entity.

Permanently transformed plant entities with increased PTGS may be virus resistant. PTGS may be suppressed in other plants to allow increased expression of a transgene for any of a variety of reasons, including improvement of plant health, adaptation to certain growing conditions, producing of a novel nutrient or vaccine, and production of a protein later purified for medical or industrial uses. Finally, the PTGS-regulatory methods of the present invention may be used to induce PTGS of a particular gene, for instance by introducing a construct encoding dsRNA for a portion of the gene, thereby offering a novel method of producing knockout plants.

The following examples are provided only to illustrate certain aspects of the invention and are not intended to embody the total scope of the invention or any aspect thereof. Variations of the exemplary embodiments of the invention below will be apparent to one skilled in the art and are intended to be included within the scope of the invention.

EXAMPLES

Example 1

Nucleotide Sequence of Sorghum Mosaic Virus

SrMV is a member of the genus Potyvirus and can cause mosaic disease and yield loss in poaceous plants such as sugarcane and sorghum (Shukla et al., 1994). A 2.0-kb region located at the 3'end of the SrMV strain H genomic RNA which encompasses the 3'untranslated region, the complete open reading frame for the coat protein and part of the NIb ORF has been previously sequenced(Yang and Mirkov, 1997). The remaining part of the SrMV genomic RNA has been sequenced in the present invention from overlapping RT-PCR products. From the combined sequences, a 9,581 bp consensus was derived that contains a continuous ORF encoding a 3079 amino acid putative polyprotein with ten gene products typical for members of the genus Potyvirus (Ingelbrecht et al., in preparation). The SrMV polyprotein consensus sequence was compared to that of Tobacco etch virus (TEV-HAT), Maize dwarf mosaic virus (MDMV-Bu), Plum pox virus (PPV-D) and Pea seed-borne mosaic virus (PSbMV-D) in a multiple sequence alignment using Clustal X. Based on this alignment, putative proteolytic cleavage sites were positioned in the SrMV polyprotein. (See FIG. 1.) A novel nucleic acid (SEQ. ID. NO. 1) encoding a novel SrMV P1/HC-Pro protein (SEQ. ID. NO. 2) was developed.

Example 2

SrMV P1/HC-Pro Reverses PTGS

The potyviral HC-Pro is a multifunctional protein and harbors at least 3 functional domains. The N-terminal part contains a highly conserved KITC motif and is involved in aphid transmission (Thornbury et al., 1985; Atreya and Pirone, 1991). The central part is required for long distance movement and virus amplification (Cronin et al., 1995; Kasschau et al., 1997) while the C-terminal part represents a papain-like proteinase involved in polyprotein processing (Carrington et al., 1990). In addition, potyviral HC-Pro is the determinant of potyviral synergistic interactions with other viruses (Pruss et al., 1997).

Potyviral HC-Pro can reverse the effects of PTGS in tissues that were previously silenced. This suppression phenotype has been observed for the potyviral HC-Pro protein of three different potyviruses, TEV, PVY and PSbMV, suggesting that this particular function of potyviral HC-Pro may be conserved among different potyviruses (Voinnet et al., 1999). From this combined with the presence of conserved amino-acid sequence motifs in the SrMV HC-Pro, it was postulated that the SrMV HC-Pro might also act as a suppressor of PTGS in sugarcane. However, the suppressor ability of SrMV HC-Pro could not be assumed based on sequence similarity alone and experiments were required to determine if suppressor activity was exhibited in sugarcane and the extent of such suppression.

Reversal of PTGS by SrMV P1/HC-Pro was demonstrated by retransforming a plant which is posttranscriptionally silenced for the CP transgene (Ingelbrecht et al., 1999, plant #16). The silenced plant #16 had originally been generated by selection on bialaphos. Embryogenic callus generated from plant # 16 was therefore retransformed with either nptII alone or with nptII and SrMV P1/HC-Pro, and transgenic plants were selected on geneticin. As shown in the Northern blot analysis of the CP gene in FIG. 2, in 5 of the 6 plants retransformed with nptII and SrMV P1/HC-Pro, PTGS has been suppressed and the steady state levels of the CP mRNA are equivalent to the levels seen in a plant that is not silenced (in FIG. 2, NS=plant #463 of Ingelbrecht et al., 1999). No such reversal was seen in plants retransformed with nptII alone. Southern and Northern analysis of nptII and SrMV P1/HC-Pro on these plants revealed that the one plant retransformed with nptII and SrMV P1/HC-Pro in which PTGS was not reversed was only transgenic for nptII (data not shown).

Example 3

The Yeast Two-Hybrid System

The yeast two-hybrid system has become a powerful tool for the study of protein-protein interactions in vivo. It can also be used to search an expression library for proteins that interact with a target protein. This latter application is being increasingly used with success in both animal (Kleiman and Manley, 1999) and plant systems (Kohalmi et al., 1998; Gindullis et al., 1999). Currently, high throughput two-hybrid procedures are being developed to catalogue protein-protein interactions on a genome-wide scale (Walhout et al., 2000).

Before embarking on a screen, it is useful to study the behavior of the target protein, termed bait, in the yeast cells. For example, one should demonstrate that the bait protein by itself does not activate transcription of the marker genes that are used in the selection and screening procedures. False positives can still be encountered following this precaution, but the great majority of these can be eliminated in subsequent steps. Finally, protein-protein interactions identified in the yeast cells may be verified via independent experimental procedures, preferably in the original biological system or a physiologically equivalent environment.

A yeast two-hybrid screening procedure typically consists of the following steps:

1) Subclone the coding region of the target protein into a LexA or GAL4 binding domain vector to create a bait. In an example of the present method this bait is the SrMV HC-Pro sequence cloned into pHYBLexZeo to generate pIV-ING1281 or SrMV P1 cloned into pAS2 to generate pIV-ING1088-6.

2) Transform the bait into the yeast reporter strain to verify that the expressed protein does not activate the reporter gene(s) by itself and is not toxic to the yeast cells.

In an example of the present method the yeast strain L40 is transformed with either pIVING1168, pIVING1281, or pIVING1088-6 alone, and also co-transformed with either a pGAD424 derivative (pIVING1154) that lacks an insert, empty pHYBLexZeo, or pHYBLexZeo containing a non-specific bait (lamin). These sets of transformed yeast strains function as negative controls for the screening procedures as known in the art.

3) Subclone a cDNA library of sequences into a GAL4 activator domain vector to create a library of prey. In an example of the present system, the cDNA library is derived from a transgenic sugarcane plant that displays PTGS (Ingelbrecht et al., 1999, plant #16) and is cloned into a modified pGAD424 derivative (pIVING1154), which constitutes the prey.

4) Transform the yeast reporter strain carrying the bait plasmid with the cDNA/prey library.

5) Screen yeast bait and prey co-transformed colonies for expression of a reporter gene that is fused to a GAL4 activated promoter. In an example of the present system, the yeast strain L40 contains reporter constructs for expression of a β-galactosidase gene, as well as a reporter construct for the HIS gene. Cells in which bait and prey fusion proteins interact in the yeast nucleus will grow on minimal media in the absence of histidine and will produce β-galactosidase enzyme activity at levels elevated from the negative control cells.

6) Verify positive interactions of co-transformants and eliminate false positives by reestablishing and retesting yeast strains, testing yeast strains which only contain the previously identified prey construct and testing the prey construct with empty bait or bait that contains a non-specific protein (such as lamin). If the prey construct activates transcription of a reporter gene that is under regulation of a GAL4-inducible promoter under any of the above conditions, the prey may be considered a false positive.

This method, as used in the examples of the present system, may be used to isolate host proteins from sugarcane and other plants that are involved in PTGS using the HC-Pro and P1 proteins from SrMV or other proteins involved in PTGS as bait. Experiments using a library-scale yeast two-hybrid screen with SrMV HC-Pro as bait have identified 441 interacting proteins. At least 12 of these (including a protein with high similarity to a viral RNase H referred to herein as the "RNase H-like protein") have been confirmed to be true interactors. Additional proteins involved in PTGS, such as a novel sugarcane 14-3-3 protein, have also been identified using the above method based on their ability to interact with the RNase H-like protein used as bait.

Example 4

Self-Interaction with HC-Pro or P1 in a Yeast Two-Hybrid System

The yeast two-hybrid method of this invention may be used to identify proteins from sugarcane that interact with HC-Pro or P1 of SrMV. The two-hybrid procedure is based on the reconstruction of a functional transcriptional activator such as GAL4 or LexA, whose DNA binding domain (DBD) and transcription activation domain (AD) are expressed on two different vectors (Fields and Song, 1989). In the present example, the bait protein, i.e. the SrMV HC-Pro, was fused to the DNA-binding domain and the cDNA library was constructed in the activation domain vector, which produces the prey. These vectors were introduced into the yeast strain L40, which has an endogenous β-galactosidase (lacZ) reporter gene and the nutritional marker HIS3 for selection.

A 1.4-kb RT-PCR fragment encompassing the complete open reading frame of HC-Pro was amplified from SrMV virion particles and subcloned in pCR4-TOPO by T/A cloning (Invitrogen, Carlsbad, Calif.), yielding pIVING1148-1. The complete HC-Pro ORF was cloned as a fusion protein into the two-hybrid vectors pHYBLexZeo (bait) and pGAD424 (prey), yielding the plasmids pIVING1281 and pIVING1168, respectively. The P1 ORF was subcloned as a 0.78-kb fragment in pAS2 yielding pIVING1088-6. The vector-insert junctions were confirmed by sequencing for all constructs.

Figure 3:
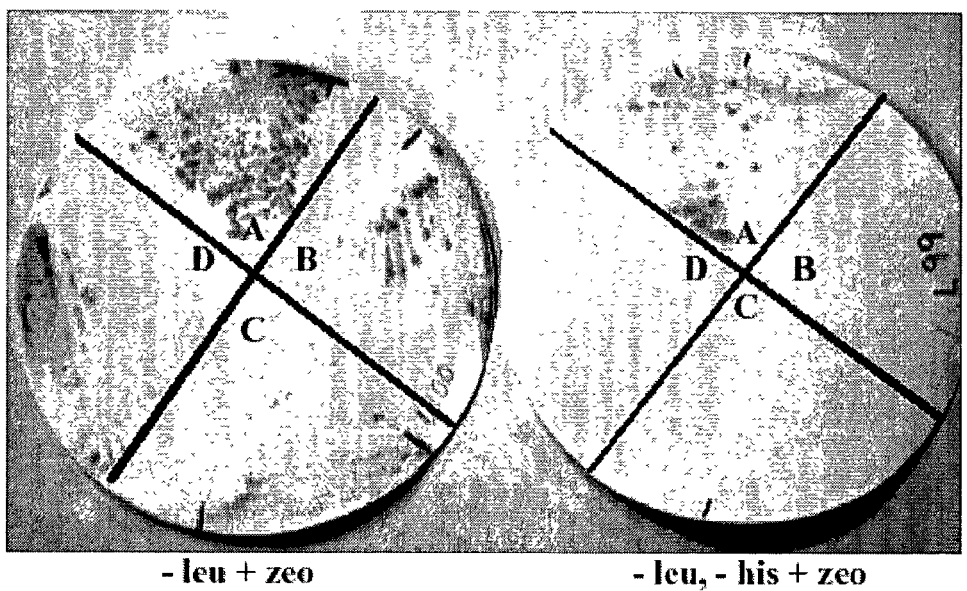
FIG. 3 is a β-galactosidase filter lift assay on L40 yeast transformed with various DNA binding and activation domain constructs and grown on media that does not select for interactions (−leu +zeo) or media that does select for transformation and interaction (−leu, −his +zeo); where the region labeled "A" represents yeast transformed with SrMV HC-Pro bait+SrMV HC-Pro prey; the region labeled "B" represents yeast transformed with SrMV HC-Pro bait+empty prey; the region labeled "C" represents yeast transformed with lamin bait+SrMV HC-Pro prey; and the region labeled "D" represents yeast transformed with empty bait+SrMV HC-Pro prey; although the figure is presented in black and white, growth in the regions marked A on both plants appears blue while, on the −leu +zeo plate, growth in regions B-D appears red.

Recent studies have shown that potyviral HC-Pro proteins can interact with themselves in a yeast two-hybrid system (Urcuqui-Inchima et al., 1999; Guo et al., 1999), in agreement with an earlier proposal that the potyviral HC-Pro is biologically active as a homodimer (Thornbury et al., 1985). The ability of the SrMV HC-Pro for self-interaction was tested in the present example. It was also verified that the SrMV HC-Pro bait construct does not activate transcription of the lacZ gene, either by itself or in combination with empty bait or prey vectors. These latter experiments were also conducted for the P1 bait construct pIVING1088-6. As shown in FIG. 3, the SrMV HC-Pro does interact with itself (A) in the two-hybrid system demonstrating the functionality of this construct. Secondly, no lacZ expression can be observed in combination with either empty prey (B) or empty bait (D) vectors or a bait vector containing a non-specific protein (lamin; C). Therefore, SrMV HC-Pro does not activate transcription by itself and can be used as bait to screen for interacting proteins. Similar results were obtained for the SrMV P1 bait construct (data not shown).

Example 5

Development of a cDNA Library From Silenced Sugarcane

The development of SrMV-resistant sugarcane plants via transformation with an untranslatable form of the capsid protein sequence has been previously described and it has been demonstrated that the underlying resistance mechanism is related to PTGS (Ingelbrecht et al., 1999). As described in Ingelbrecht et al., 1999, plant #16 is a recovery plant that is immune to infection with SrMV after recovery from the initial infection and is posttranscriptionally silenced for the CP transgene. Although the CP transgenes are actively transcribed, the CP steady-state mRNA level is below the detection limit on an RNA gel blot (See Example 2 and FIG. 2).

Figure 4:
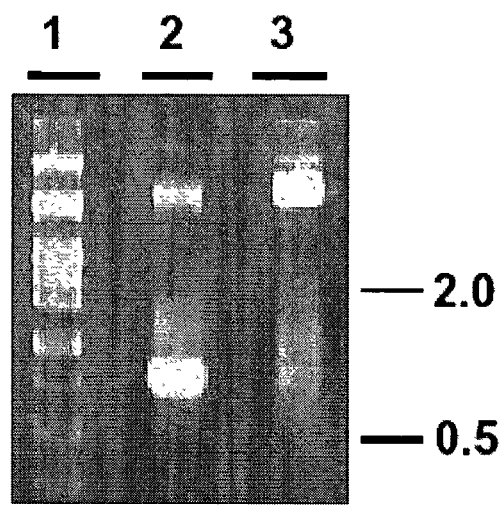
FIG. 4 is a gel analysis of the cDNA library cloned in pIVING1154; where Lane 1 contains a λPstI size marker; Lane 2 contains a lower band of 0.8 kb which is the CP coding region amplified from the plasmid cDNA library and a top band of 6.6-kb which is the plasmid vector; and Lane 3 contains a SfiI digest of plasmid library showing the 6.6-kb vector and inserts visible as a smear with size range between 0.5 and 2.0 kb.

Using poly(A)+ RNA from silenced leaf tissue of this plant a cDNA fusion library was constructed in the prey vector pIVING 1154 using the SMART™ PCR cDNA library construction kit (offered by Clontech, Palo Alto Calif., a part of Beckton Dickinson, Franklin Lakes, N.J.). To create the vector p1VING1154, pGAD424 was modified to allow directional cloning of the cDNA into asymmetric SfiI sites. The library has an estimated $1.6 \times 10^6$ primary clones. As shown in FIG. 4, the inserts range between 0.5 to 2.0 kb with an average size of about 0.8 kb. Also, a 0.8-kb fragment containing the CP coding sequence could be readily amplified from the plasmid cDNA library indicating that low abundance mRNAs are represented.

Example 6

Library Scale Two-Hybrid Screen with HC-Pro Bait

The yeast strain L40 containing the SrMV HC-Pro bait construct was transformed with the prey CDNA library representing the equivalent of approximately $1.6\times10^6$ primary *E. coli* clones (see Example 4). About 77 million primary yeast transformants were plated on selective media (−leucine, −histidine +zeocin) and 776 yeast colonies were recovered by the fourth day of growth. Of these, 441 showed a range of light to heavy blue staining in the standard β-galactosidase colony-lift filter assay. To date, all of these double transformants have been colony purified, and all of the prey plasmids have been isolated. A RNase H-like protein, a RING zinc finger protein and LRR transmembrane protein kinase have been identified among the true positives. Some results of this screen and additional screens with SrMV P1 or RNase H like-protein as the bait are depicted in Table 1.

TABLE 1

| Bait (DBD) | Prey (AD) | Interaction |
|---|---|---|
| SrMV HC-Pro | SrMV HC-Pro | ++ |
| SrMV P1 | SrMV P1 | −/+ |
| SrMV HC-Pro | SrMV P1 | − |
| SrMV P1 | SrMV HC-Pro | − |
| SrMV HC-Pro | RNase H-like prot. | +++ |
| RNase H-like prot. | SrMV HC-Pro | +++ |
| SrMV P1 | RNase H-like prot. | − |
| RNase H-like prot. | RNase H-like prot. | +++ |

A −/+ plus designates that very light blue staining was observed only after a 24 hour incubation. +++ designates that strong blue staining was seen in less than 30 minutes, and ++ designates strong blue staining in less than 3 hours. The RNase H-like protein self interaction may indicate that the protein functions as a homodimer.

Example 7

RNase H-Like Protein

Figure 5:
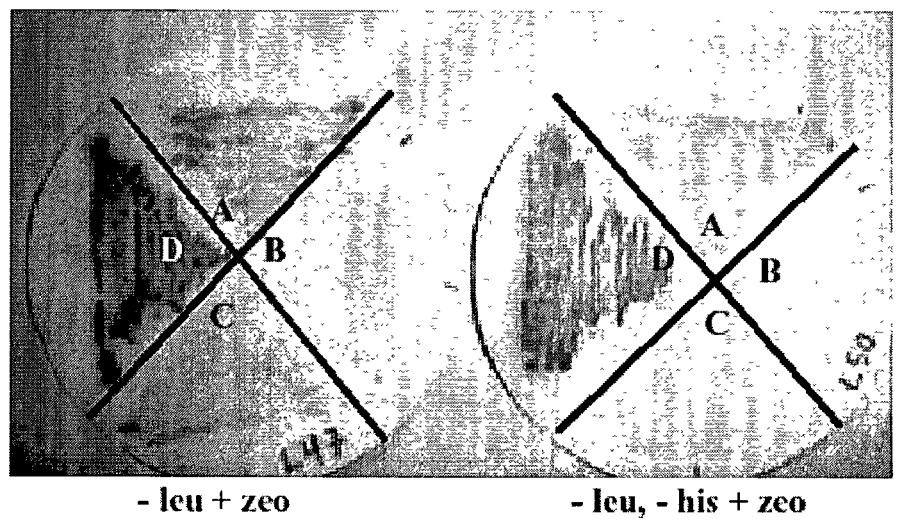
FIG. 5 is a β-galactosidase filter lift assay on L40 yeast transformed with various DNA binding and activation domain constructs and grown on media that does not select for interactions (−leu +zeo) or media that does select for transformation and interaction (−leu, −his +zeo); where the region labeled "A" represents yeast transformed with SrMV HC-Pro bait+SrMV HC-Pro prey; the region labeled "B" represents yeast transformed with empty bait+RNase H-like protein prey; the region labeled "C" represents yeast transformed with lamin bait +RNase H-like protein prey; and the region labeled "D" represents yeast transformed with SrMV HC-Pro bait+RNase H-like protein prey; although the figure is not presented in color, the regions marked A and D on both plates appear blue, while the regions marked B and C on the −leu +zeo plate appear red.
Figure 11A:
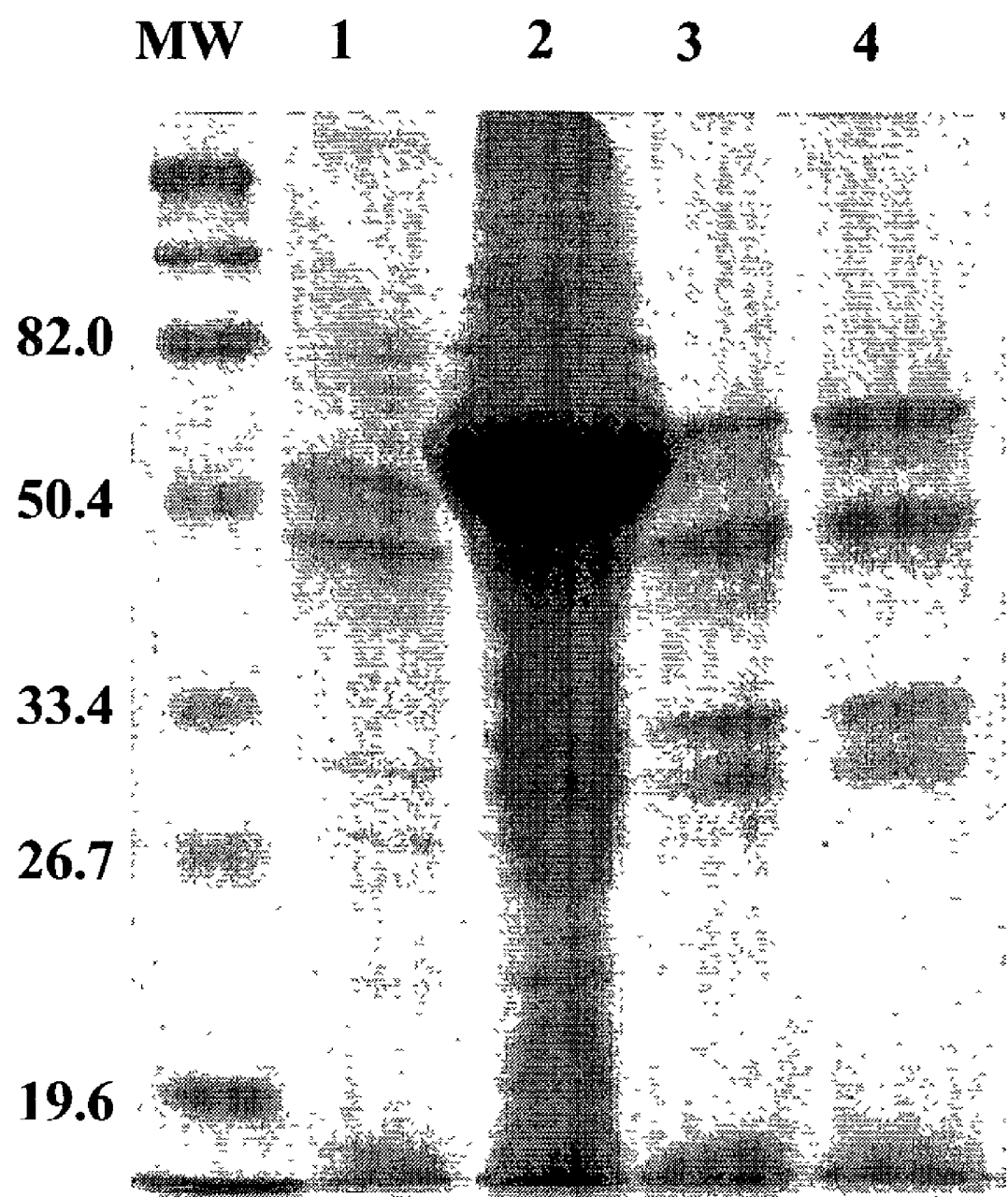
FIG. 11A shows a 12% PA, CB stained gel.
Figure 11B:
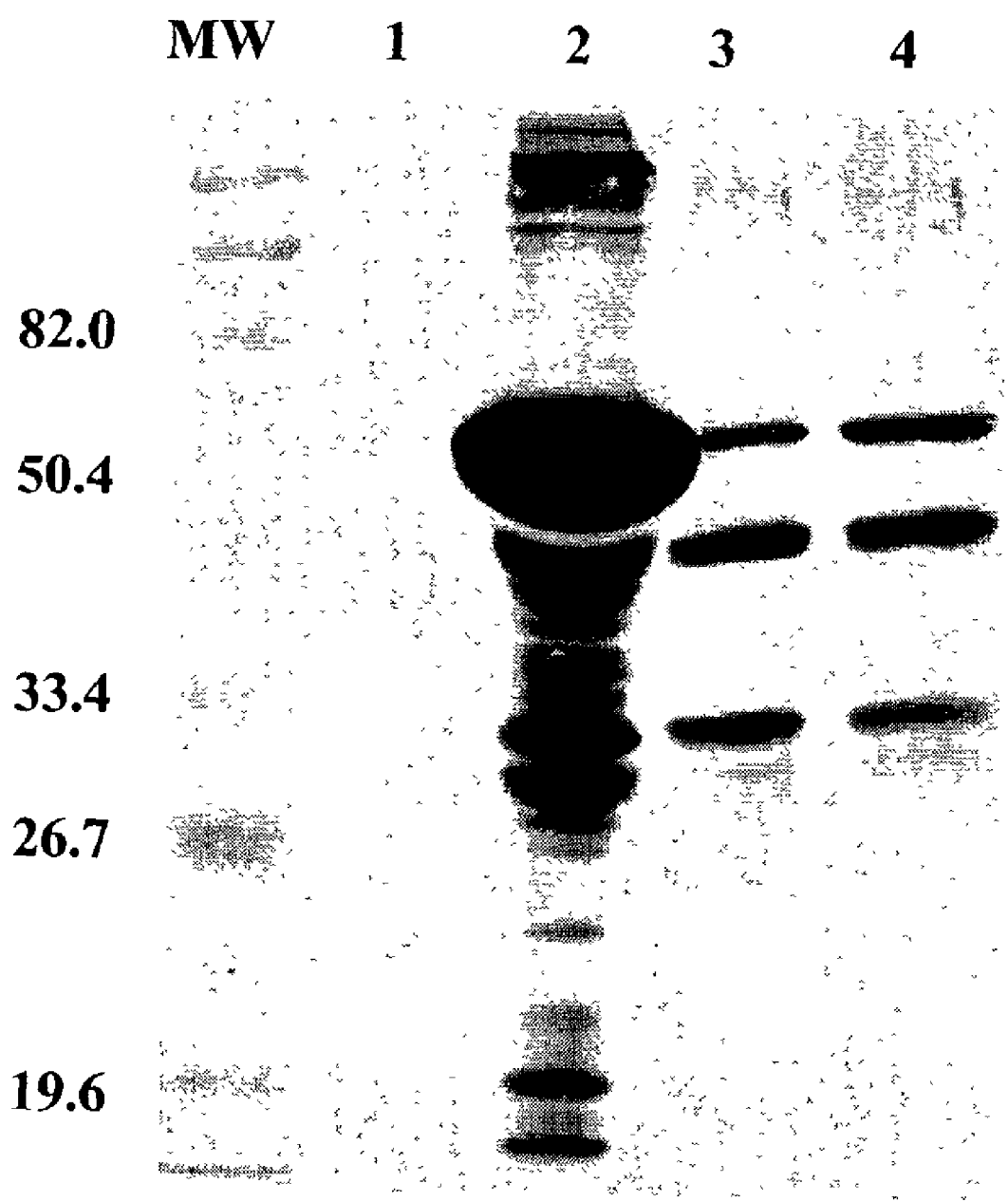
FIG. 11B shows a Large S-AP probed blot; in parts of FIG. 10, the molecular weight lane is indicated as "MW", lane 1 contains the *E. coli* expression product of Bugbuster™ (Novagen, Madison, Wis., affiliate of Merck KgaA, Darmstadt, Germany) Insoluble pET30 with no insert; lane 2 contains the *E. coli* expression product of Bugbuster™ Insoluble pET30 with an SrMV HC-Pro insert; lane 3 contains one preparation of Ni column purified *E. coli* expression product of Bugbuster™ Insoluble pET30 with an SrMV HC-Pro insert; and lane 4 contains a second preparation of Ni column purified *E. coli* expression product of Bugbuster™ Insoluble pET30 with an SrMV HC-Pro insert.
Figure 12:
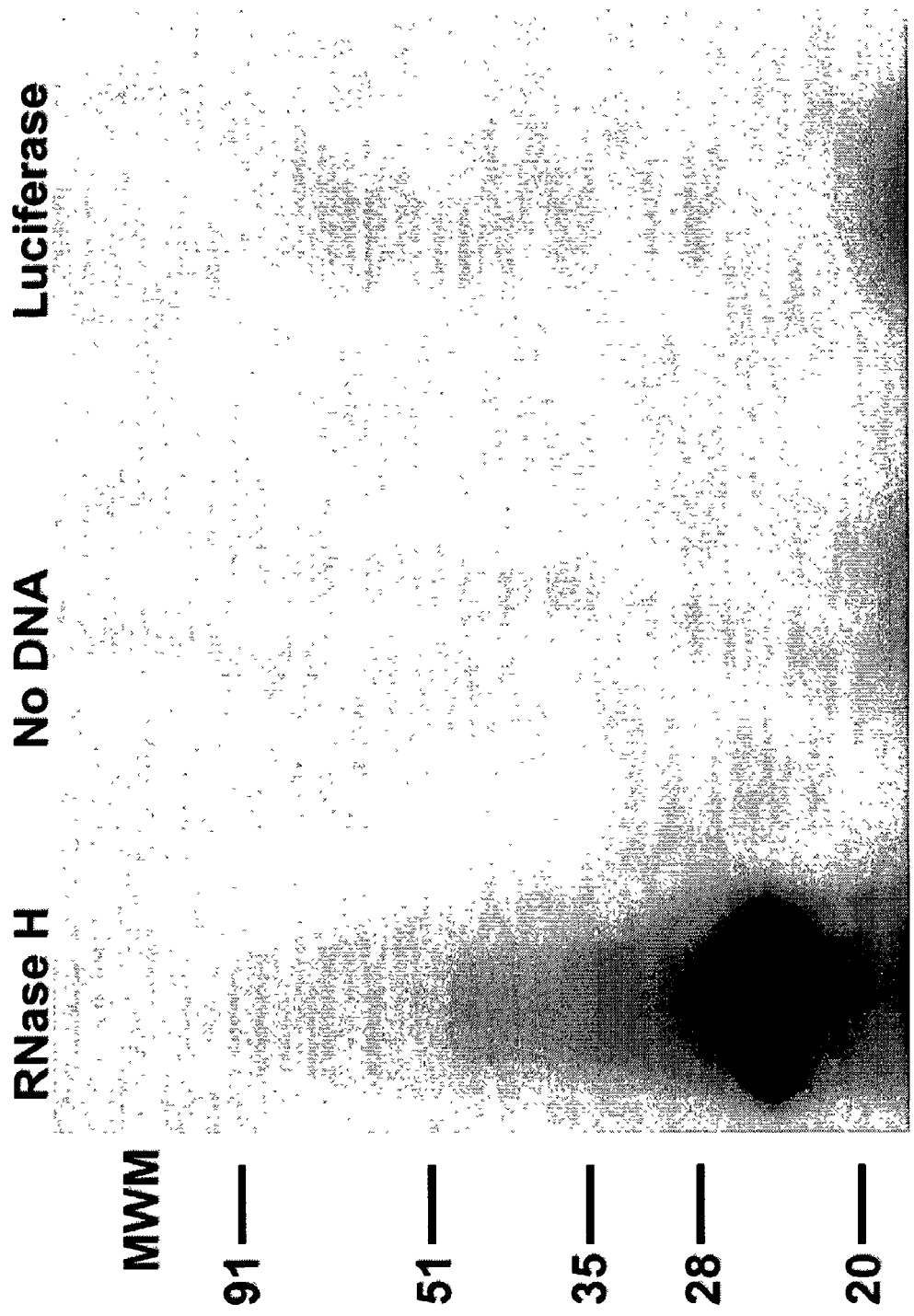
FIG. 12 shows a two hour exposure of a 15% SDS PAGE gel containing RNase H-like protein (lane labeled "RNase H") labeled with $^{35}$S Cysteine according to the present invention; control lanes are provided in which no DNA was used in the preparation procedure (lane labeled "No DNA"), and in which Luciferase DNA was used (lane labeled "Luciferase"); molecular weight markers are indicated.

One of the prey plasmids that was recovered during the experiments of Example 5 was retransformed into the SrMV HC-Pro bait yeast strain to reconfirm activation of the reporter genes. The plasmid encodes a protein with approximately 40% identity to a viral RNase H. This protein has been recovered several times using the methods of these examples. As shown in FIG. 5, the interaction with HC-Pro is very strong (D) and there is no interaction in combination with an empty bait plasmid or with a lamin bait plasmid (B and C, respectively). Furthermore, the RNase H-like gene is in the correct reading frame with respect to the fusion protein, so this is a true interactor. The cDNA sequence (SEQ. ID. NO. 3) for a nucleic acid encoding the RNase H-like protein and its amino acid sequence (SEQ. ID. NO. 4) are provided in FIG. 6.

Example 8

RING Zinc Finger Protein That Interacts With HC-Pro

Another protein identified as a true positive in HC-Pro interaction screens is a RING zinc finger protein. A partial cDNA sequence of a nucleic acid encoding this protein is provided in FIG. 7A (SEQ. ID. NO. 5). The encoded amino acid sequence is included as FIG. 7B (SEQ. ID. NO. 6). The nucleic acid sequence is sufficient to identify nucleic acids encoding the protein, but likely lacks approximately 300 bp at the 5' end in the figure. However, because a protein encoded by the possibly truncated nucleic acid sequence was identified in a two-hybrid screen, a nucleic acid with the sequence provided must encode a sufficient portion of the protein to allow interaction with SrMV HC-Pro. With the information disclosed in this invention, it is possible for a person skilled in the art to isolate the full length cDNA and protein sequence.

Example 9

LRR Transmembrane Protein Kinase

Another protein identified as a true positive in SrMV HC-Pro yeast two-hybrid screens is an LRR transmembrane protein kinase. A partial cDNA sequence of a nucleic acid encoding this protein is provided in FIG. 8A (SEQ. ID. NO. 7). The encoded amino acid sequence is included in FIG. 8B (SEQ. ID. NO. 8). The sequence is sufficient to identify nucleic acids encoding the protein, but likely lacks approximately 1 kb at the 5' end in the figure. However, because a protein encoded by the possibly truncated nucleic acid sequence was identified in a two-hybrid screen, a nucleic acid with the sequence provided must encode a sufficient portion of the protein to allow interaction with SrMV HC-Pro. With the information disclosed in this invention, it is possible for a person skilled in the art to isolate the full length cDNA and protein sequence.

Example 10

Library Scale Two-Hybrid Screen with RNase H-Like Protein as Bait

A library scale two-hybrid screen similar to that of Example 5 was conduced using the same prey library (described in Example 4) with the RNase H-like protein as bait. Using the RNase H-like protein as bait, at least two true positives for prey/host proteins were identified and further characterized. The results of some of these assays as well as assays with SrMV HC-Pro and SrMV P1 as bait are depicted in Table 2.

TABLE 2

| Bait (DBD) | Prey (AD) | Interaction |
|---|---|---|
| SrMV HC-Pro | SrMV HC-Pro | ++ |
| RNase H-like prot. | SrMV HC-Pro | +++ |
| SrMV P1 | RNase H-like prot. | − |
| RNase H-like prot. | RNase H-like prot. | +++ |
| RNase H-like prot. | Sugarcane 14-3-3 | +++ |
| SrMV HC-Pro | Sugarcane 14-3-3 | − |
| SrMV P1 | Sugarcane 14-3-3 | − |

A −/+ designates that very light blue staining was observed only after a 24 hour incubation. +++ designates that strong blue staining was seen in less than 30 minutes, and ++ designates strong blue staining in less than 3 hours.

Example 11

Sugarcane 14-3-3 Protein

One protein identified through its ability to interact with the RNase H-like protein is a sugarcane 14-3-3 protein. The sequence of a nucleic acid encoding the sugarcane 14-3-3 protein is provided in FIG. 9A (SEQ. ID. NO. 9). The encoded amino acid sequence is provided in FIG. 9B (SEQ. ID. NO. 10). The role of another 14-3-3 protein in signal transduction in the dicot *Arabidopsis* has recently been described in Sebnke et al., 2002. A similar role in monocots is suggested by the disclosed in this invention. Specifically, 14-3-3 proteins exhibit a phosphorylation-dependent association with proteins in dicots. The RNase H-like protein of the present invention contains a seine with a 99.1% chance of being phosphorylated. This seine is also located in a good consensus 14-3-3 protein client-binding site. More specifically, the putative phosphorylation/binding site is VIQNpSPPDL (wherein "pS" designates phosphoserine) (SEQ. ID. NO. 13 beginning at amino acid 48 of the protein in FIG. 9B. Binding of sugarcane 14-3-3 and the RNase H-like protein in order to achieve a functional dimer (or as part of a functional complex containing other proteins) is also suggested by the absence of DNase or RNase activity of either protein in isolation. As shown in Table 2, 14-3-3 does not interact noticeably with SrMV HG-Pro or SrMV P1.

Example 12

RING Zinc Finger Protein that Interacts with RNase H-Like Protein

Another protein identified as a true positive in RNase H-like protein interaction screens is a RING zinc finger protein. This is not the same RING zinc finger protein identified as interacting with SrMV HC-Pro. A partial cDNA sequence of a nucleic acid encoding this protein is provided in FIG. 10A (SEQ. ID. NO. 11). The amino acid sequence encoded by the nucleic acid is provided in FIG. 10B(SEQ. ID. NO. 12)

Example 13

DNA Sequence Analyses of the Prey Genes Identified in the Two-Hybrid Screen

Prey sequences that have been verified by the above screening procedures may be DNA sequenced utilizing standard fluorescence-based thermocycle sequencing methods, and restriction maps created. This sequence information may be utilized to search the genetic databases with BLASTx and BLASTp to determine sequence similarity with known genes or proteins. In cases where similarity is clear, one may verify that the sequence under investigation is inserted in the appropriate reading frame in the prey vector. If the sequence is not in the appropriate reading frame, the prey can be considered a false positive.

Example 14

Characterization of the Prey Nucleic Acids Identified in the Two-Hybrid Screen for the Ability of Their Corresponding Proteins to Interact with SrMV HC-Pro Protein or other Bait Protein In Vitro under Physiological Conditions Although prey and bait combinations identified in the two-hybrid screen of the present invention may represent proteins which interact in yeast cells, several caveats of the assay may produce results which are not indicative of interactions that occur in planta. The yeast two-hybrid system assay requires that the bait and prey GAL4 fusion proteins both be imported into the yeast nucleus, which biochemically is a much more reducing environment than the yeast cytoplasm. This may lead to different patterns of protein folding than might otherwise occur for proteins whose operating environment is a more oxidative cytoplasm. Additionally, protein fragments placed in an unnatural position in a yeast two-hybird assay (e.g. an N term region in the C term of the fusion protein) may fail to fold or function properly because of positional effects.

Given that in vivo studies often require specialized reagents in the present method, an initial in vitro screening procedure in which potential protein interactions are verified under physiological conditions may be used to save time and expense associated with plant transformations in the case of false positives. However, it does remain possible that in vitro conditions may lack certain requirements for interaction found only in living cells and thus generate false negatives. Therefore, in some instances it may be desirable to proceed with in planta studies without or despite results in vitro. Such an approach is within the scope of the present invention.

If in vitro studies are preformed, host/prey proteins identified in the two-hybrid screen may be further tested for their ability to interact with SrMV P1 and SrMV HC-Pro or other proteins involved in PTGS in vitro under physiological conditions (i.e. pH 6.8 and 0.1 M ionic strength) as either polyhistidine, S-tag, or glutathione-s-transferase (GST) fusion-proteins. A series of vectors from Novagen, Inc. (Madison, Wis., affiliate of Merck KgaA, Darmstadt, Germany) including pET15b, pET29a,b,c and pET30a,b,c, allow the construction of N-terminal or C-terminal polyhistidine fusion proteins, which in the case of pET29 and pET30 derivatives may also contain S-tags. Pharmacia Corp. (Peapack, N.J.) also produces pGEX2, pGEX3 and pGEX4 derivatives in which GST fusion proteins may be produced. These vectors allow the specific purification of "tagged" proteins that have either polyhistidine tags (using Ni+-chelated resin), S-tags (using S-agarose), or GST-tags (using reduced glutathione-conjugated resins). Bait and prey inserts identified from the two-hybrid screen may be subcloned into one of these vectors. Other vectors encoding tag regions may also be used.

One approach is to construct two vector types, if possible, for the bait as well as for each prey that has been identified and to produce GST- and polyhistidine tagged proteins in *E. coli*. These tagged proteins may be purified with kits available from Pharmacia, Novagen, or other sources, or using methods known to the art and appropriate for the selected tag. His-S tagged SrMV HC-Pro produced in the pET30 vector purified with a Ni column is shown in FIG. 11 in lanes 3 and 4. As FIG. 11 indicates, tagged protein is produced only when an insert is present in the vector and may be largely purified using a Ni column.

Radiolabelled SrMV HC-Pro, SrMV P1, RNase H-like protein or other bait proteins of interest may be produced by translation of their corresponding transcripts in rabbit reticulocyte lysate. Using the TNS method, transcripts may be generated in a T7 in vitro transcription system or other system known to the art. Subsequent translation in the presence of S-35-labeled methionine or cysteine allows radiolabeling of the bait protein. FIG. 12 shows that RNase H-like protein produced using the above methodology is, in fact, radiolabeled. A small amount of this translated lysate may then be incubated with the tagged prey protein bound to its corresponding resin, and retention of radiolabeled bait protein may be assayed with SDS-PAGE gels and autoradiograms. Positive controls can include tagged bait protein, and negative controls can include the tags themselves, as well as the resins without any other proteins. These procedures or various modifications thereof readily determined by one skilled in the art allow one to determine whether prospective prey proteins are capable of interacting with either one or both viral proteins in vitro under physiological conditions.

Example 15

Farwestern Blots and Other Assays Indicate Interaction of Various Proteins

Figure 13:
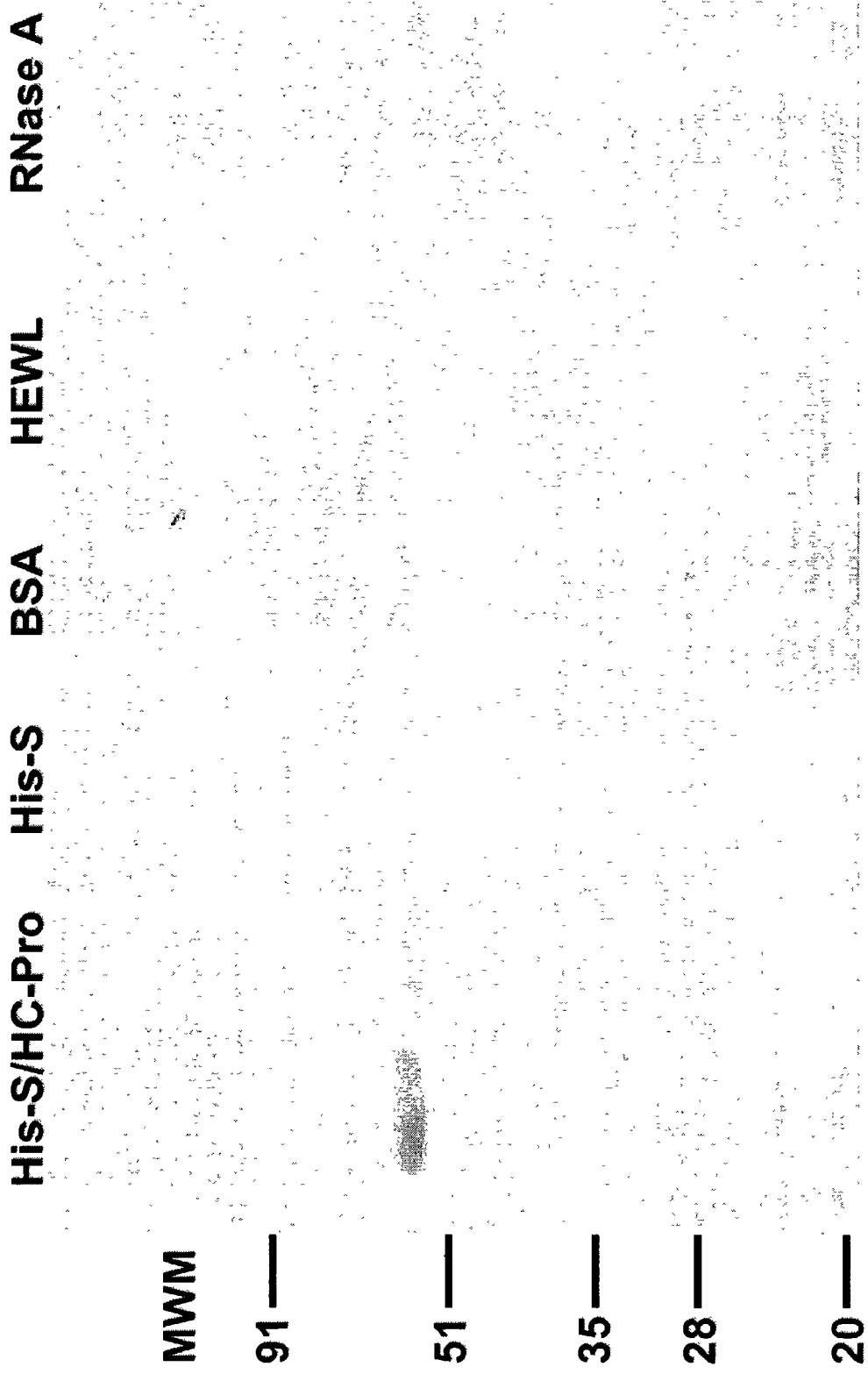
FIG. 13 shows a 32 hour exposure of a farwestern blot probed under in vitro plant cell physiological conditions with a $^{35}$S labeled RNase H-like protein transcription and translation (TNT) product; the lane labeled "His-S/HC-Pro" contains Ni column purified, His-S tagged SrMV HC-Pro protein produced in *E. coli*; the lane labeled "His-S" contains the HIS-S tag only; the lane labeled "BSA" contains untagged bovine serum albumen; the lane labeled "HEWL" contains untagged hen egg white lysozyme and the lane labeled "RNase A" contains untagged RNase A.

FIG. 13 shows a farwestern blot of His-S tagged SrMV HC-Pro probed with 35S labeled RNase H-like protein. Both proteins were produced according to the methods of the above examples. A comparison of binding of labeled RNase H-like protein to the His-S tagged SrMV HC-Pro to the various controls indicates that the interaction is specific between the two proteins and also that it occurs in conditions approximating plant physiological conditions.

Figure 14:
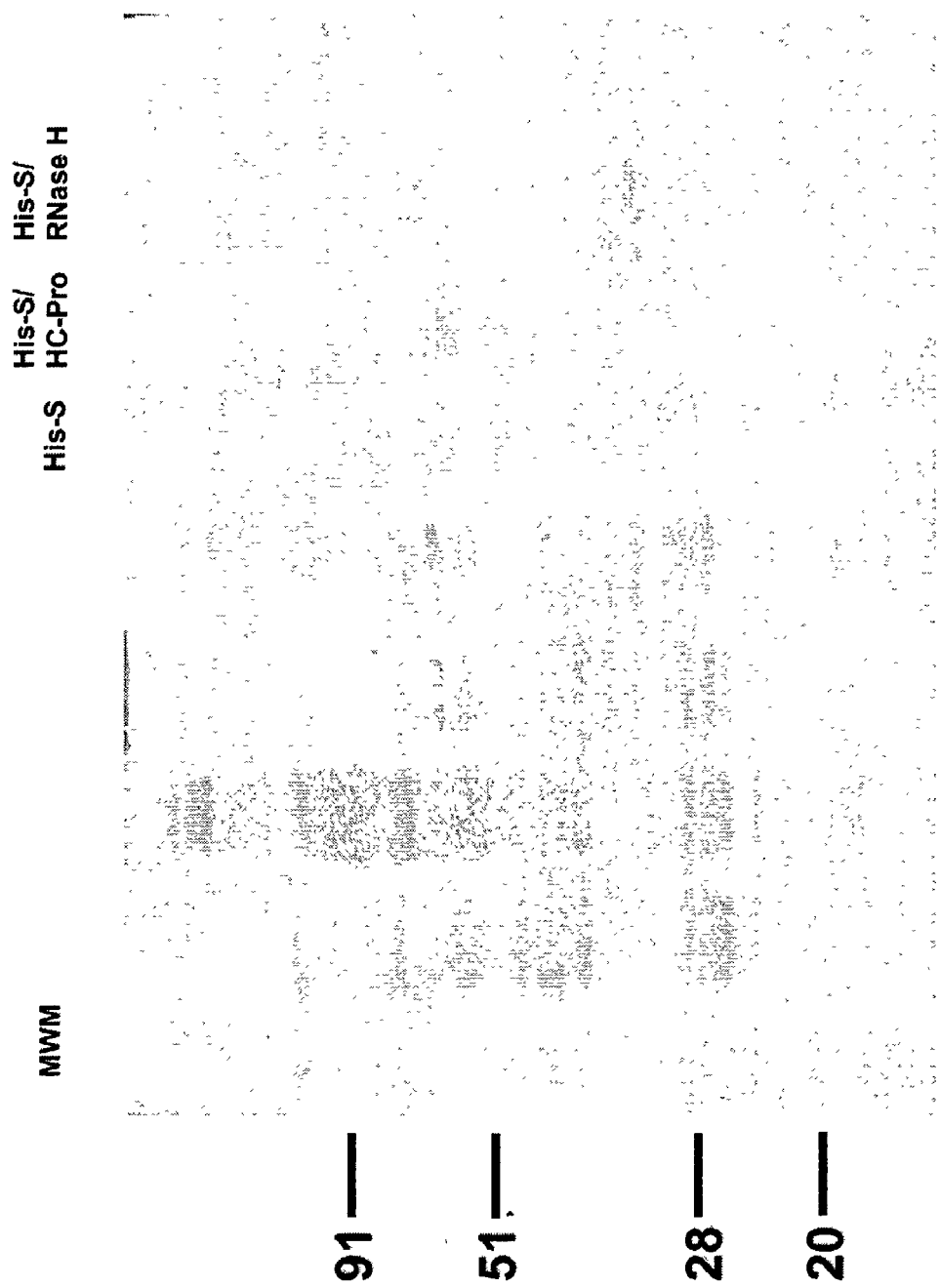
FIG. 14 shows a 6 hour exposure of a farwestern blot probed under in vitro plant cell physiological conditions with a $^{35}$S labeled RNase H-like protein transcription and translation (TNT) product; the lane labeled "His-S/HC-Pro" contains Ni column purified, His-S tagged SrMV HC-Pro protein produced in *E. coli*; the lane labeled "His-S/RNase H" contains Ni column purified, His-S tagged RNase H-like protein produced in *E. coli*; the lane labeled "His-S" contains the product in *E. coli* of the His-S tag only; the unlabeled lanes contain plant extracts which are from left to right, from: healthy sugarcane plant, SrMV infected sugarcane plant, sugarcane plant transgenic for SrMV P1/HC-Pro, sugarcane plant transgenic for delta N 12 SrMV HC-Pro.; and the lane labeled MWM contains molecular weight markers, which were used to produce the size indicators on the side of the blot.

FIG. 14 shows a farwestern blot of His-S tagged SrMV HC-Pro and RNase H-like protein and a plant extracts probed with $^{35}$S labeled RNase H-like protein. A comparison of the lanes indicates that the RNase H interacts with itself and SrMV HCPro and with other sugarcane proteins-from left to right-healthy sugarcane plant, SrMV infected sugarcane plant, sugarcane plant transgenic for SrMV P1/HC-Pro, sugarcane plant transgenic for SrMV delta N 12 HC-Pro. An extra band in the three plants expressing SrMV HC-Pro that is slightly smaller than the tagged SrMV HC-Pro may be seen in FIG. 14.

Figure 15:
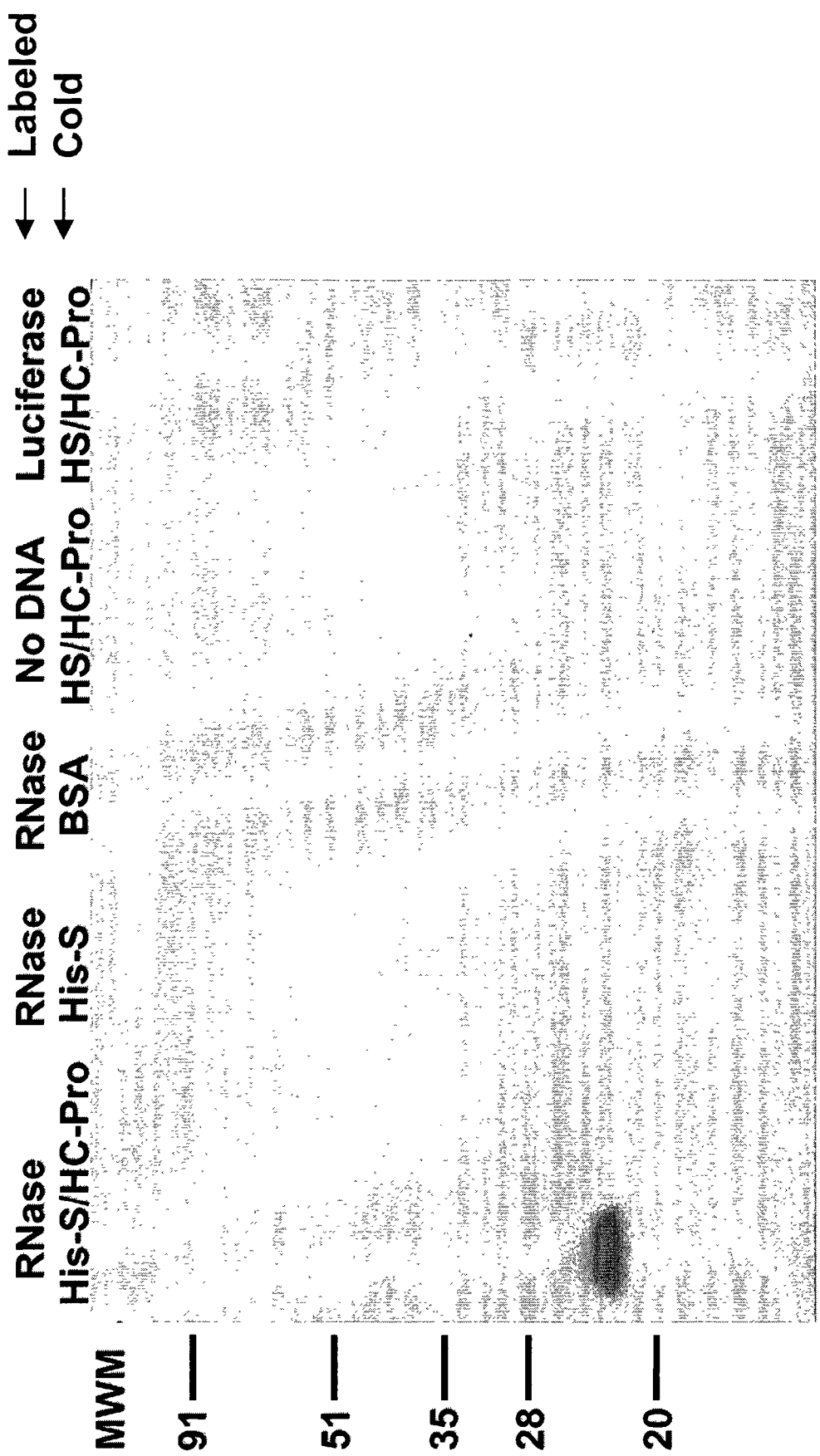
FIG. 15 shows a 32 hour exposure of a 15% SDS PAGE gel on which Ni column pull down products of a TNT 35S labeled protein/His-S tagged protein physiological incubation were run; the top lane marker indicates the source of DNA used in a TNT procedure in to obtain $^{35}$S labeled protein, where "RNase" indicates the use of RNase H-like protein cDNA, "No DNA" indicates a control in which no DNA template was provided, and "Luciferase" indicates a control in which Luciferase DNA was provided; the bottom lane marker indicates the His-S tagged product produced in *E. coli*, where "His-S/HC-Pro" or "HS/HC-Pro" indicates Ni column purified His-S tagged SrMV HC-Pro protein, "His-S" indicates the His-S tag only, and "BSA" indicates untagged bovine serum albumen.

FIG. 15 shows the results of a Ni column pull down of His-S tagged protein and its binding partner. The proteins attached to the Ni column were removed and run on an SDS PAGE gel. The results indicate that His-S tagged SrMV HC-Pro and not control proteins pulled down labeled RNase H-like protein. Label controls were not pulled down. This indicates that the SrMV HC-Pro/RNase H-like protein interaction is specific and viable under physiological conditions.

Figure 16:
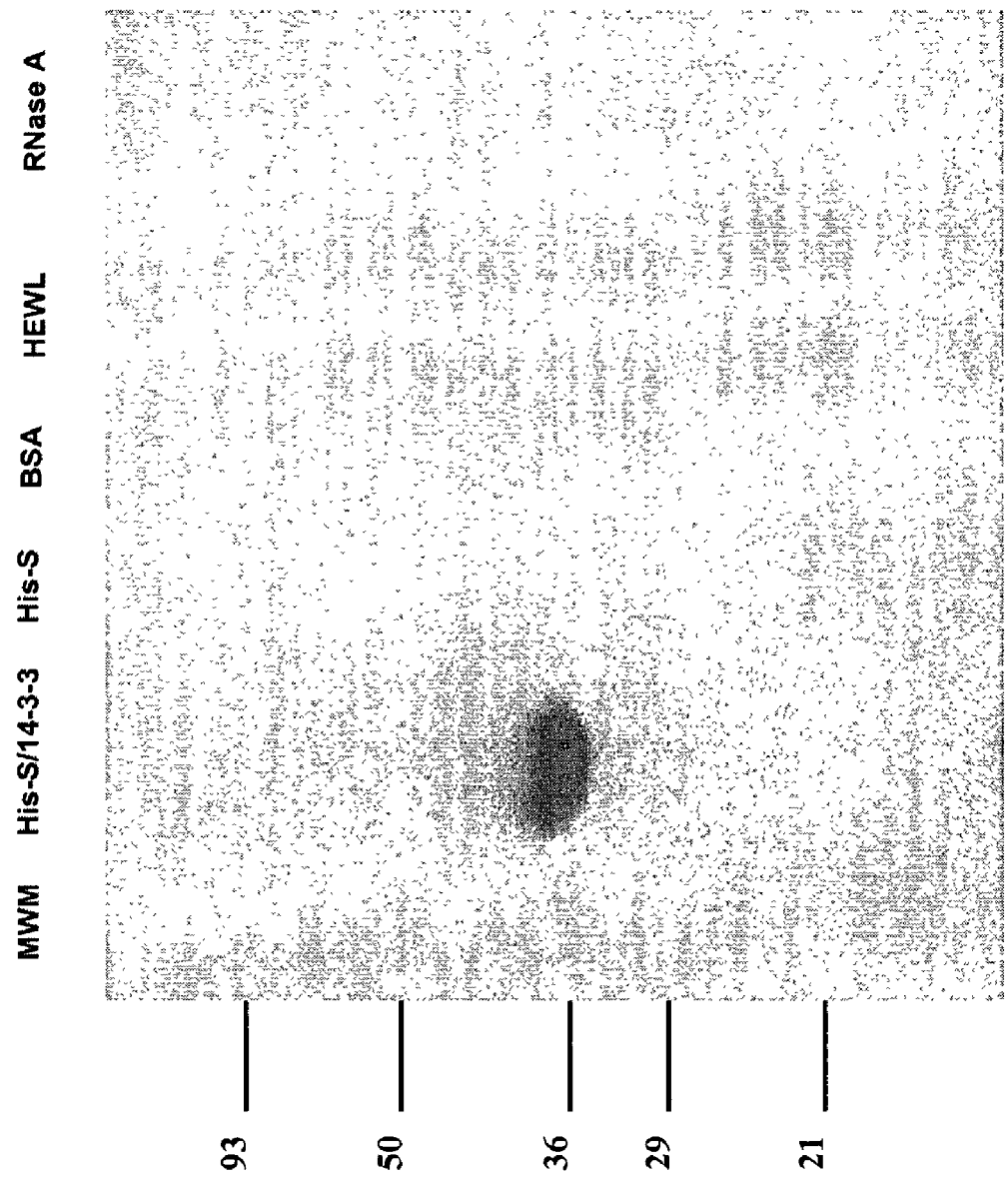
FIG. 16 shows a 3 hour exposure of a farwestern blot probed under in vitro plant cell physiological conditions with a $^{35}$S labeled RNase H-like protein transcription and translation (TNT) product; the lane labeled "His-S/14-3-3" contains Ni column purified, His-S tagged sugarcane 14-3-3 protein produced in *E. coli*; the lane labeled "His-S" contains the His-S tag only; the lane labeled "BSA" contains untagged bovine serum albumen; the lane labeled "HEWL" contains untagged hen egg white lysozyme; and the lane labeled "RNase A" contains untagged RNase A.
Figure 17:
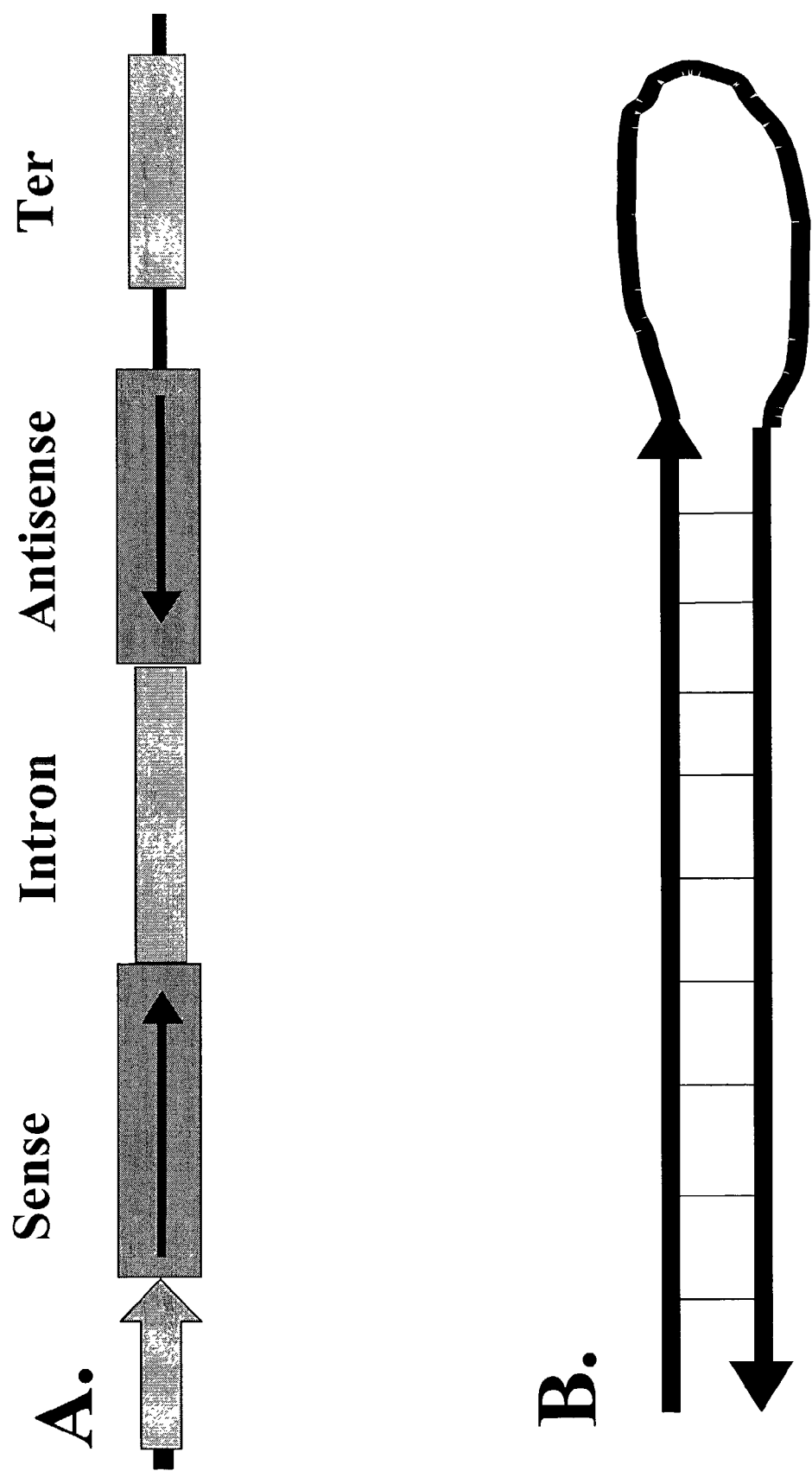
FIG. 17A depicts a DNA construct containing sense and antisense sequences in opposite directions and separated by an intron which, following transcription to mRNA, form a double strand due to sense/antisense sequence complementation shown in FIG. 17B.
Figure 18:
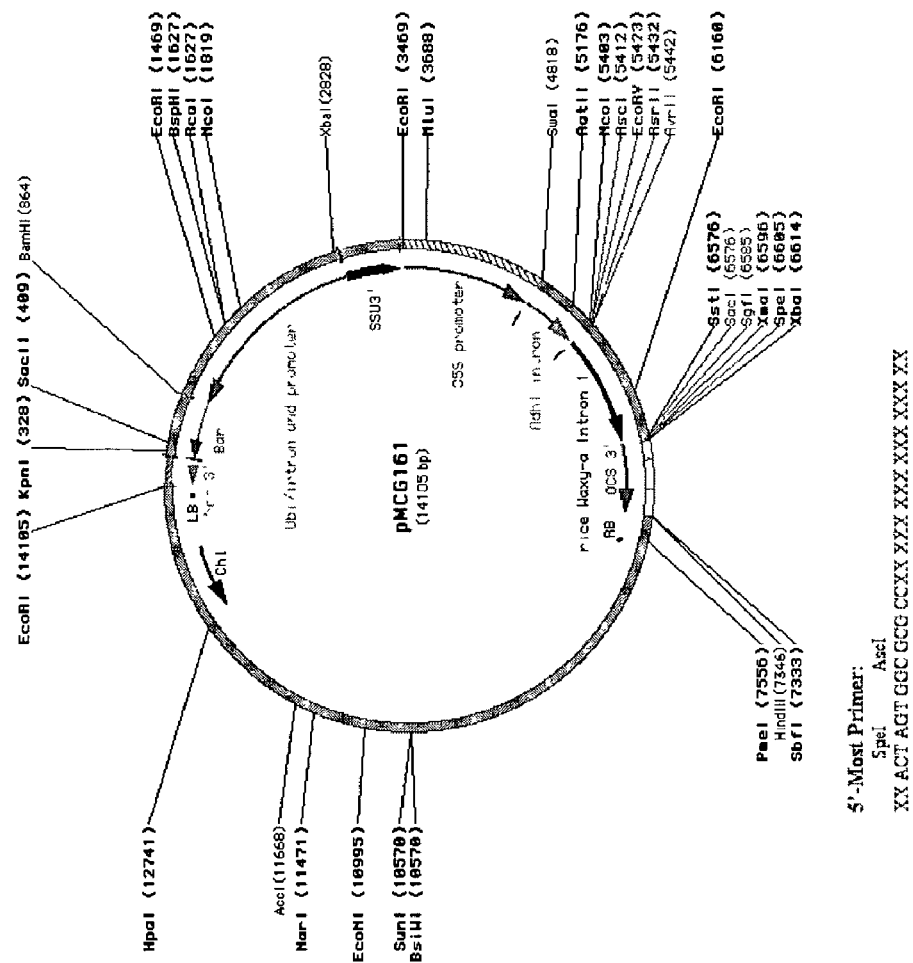
FIG. 18 depicts the pMCG161 plasmid expression vector, according to one embodiment of the present invention.
Figure 19:
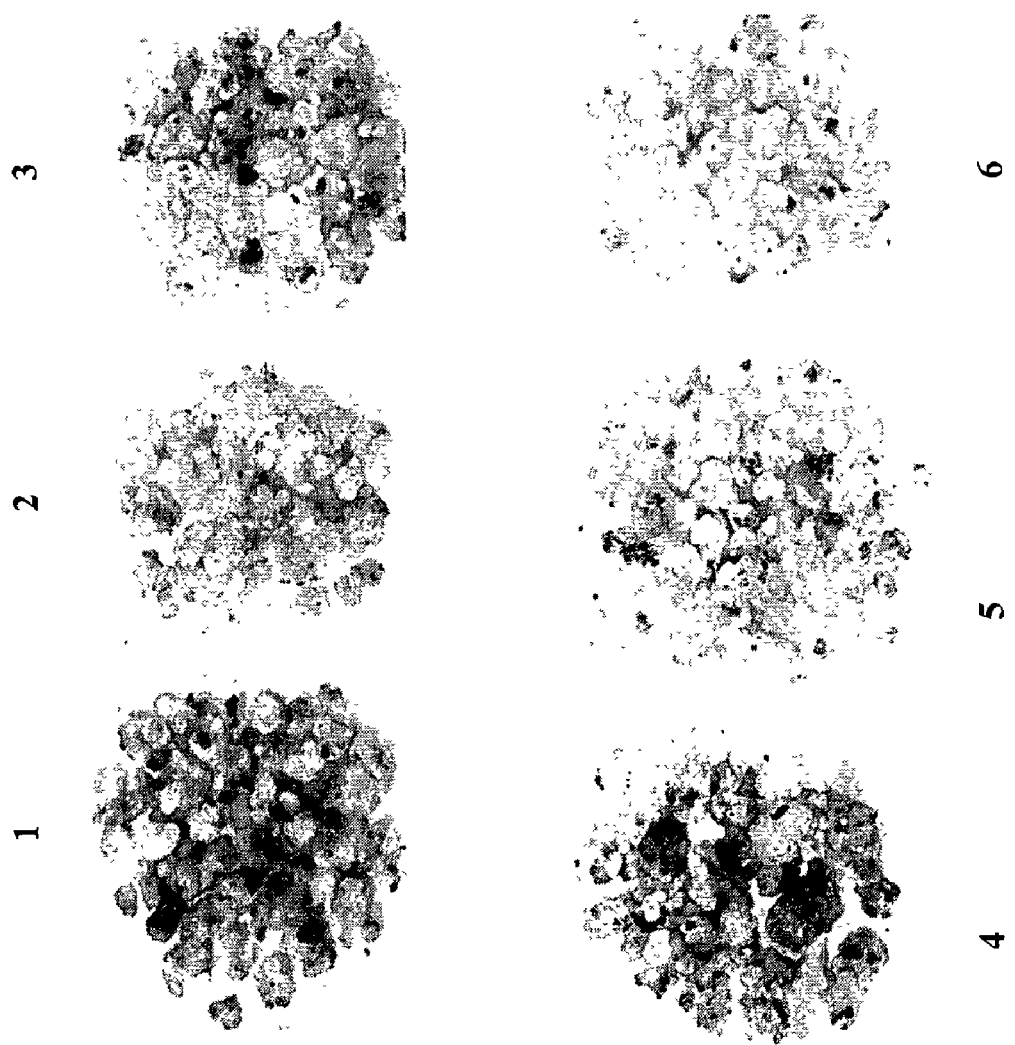
FIG. 19 depicts the results of transient expression of constructs inserted in the pMGC161 plasmid in embryonic sugarcane calli where the callus 1 is transformed with GUS under control of a Ubi promoter; callus 2 is transformed with GUS under control of a Ubi promoter and DNA that produces double stranded GUS mRNA under control of a 35Sint promoter; callus 3 is transformed with the same constructs as callus 2 and additionally with DNA that produces double stranded RNase H-like protein mRNA under control of the 35Sint promoter; callus 4 is transformed with the same constructs as callus 2 and additionally with SrMV P1/HC-Pro under the control of the Ubi promoter; callus 5 is transformed with the same constructs as callus 2 and additionally with SrMV HC-Pro-delta N 12 under control of the Ubi promoter for ease of plasmid construction to include a start ATG, the first N-terminal amino acids of the full length SrMV HC-Pro are deleted via deletion of 36 cDNA base pairs); and callus 6 is transformed with the same constructs as callus 2 and additionally with DNA that produces double stranded GFP under control of the 35Sint promoter; although the figure is not provided in color, all darker regions in the calli of the figure are blue while ligher regions are pinkish tan, as will be apparent to one skilled in the art.
Figure 20:
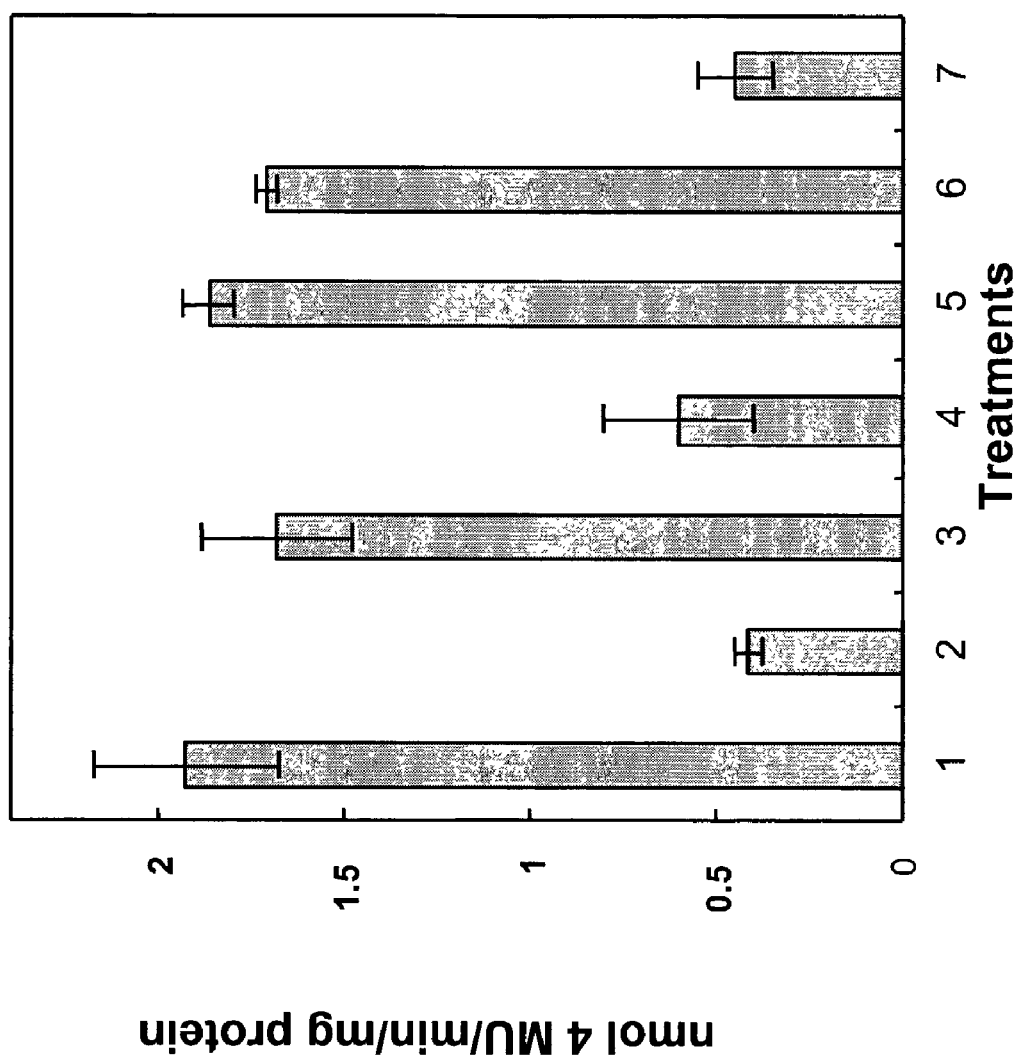
FIG. 20 is a graphical representation of three experiments such as that of FIG. 19; vertical bars represent the average of these three independent experiments while vertical line represent standard errors; treatment 1 represents transformation with GUS under control of a Ubi promoter; treatment 2 represents transformation with GUS under control of a Ubi promoter and DNA that produces double stranded GUS mRNA under control of a 35Sint promoter; treatment 3 represents transformation with the same constructs as treatment 2 and additionally with DNA that produces double stranded RNase H-like protein mRNA under control of the 35Sint promoter; treatment 4 represents transformation with the same constructs as treatment 2 and additionally with RNase H-like protein under control of the 35Sint promoter; treatment 5 represents transformation with the same constructs as treatment 2 and additionally with SrMV P1 and HC-Pro under the control of the Ubi promoter; treatment 6 represents transformation with the same constructs as callus 2 and additionally with SrMV HC-Pro-delta N 12 under control of the Ubi promoter; and treatment 7 represents transformation with the same constructs as callus 2 and additionally with DNA that produces double stranded GFP mRNA under control of the 35Sint promoter.
Figure 21:
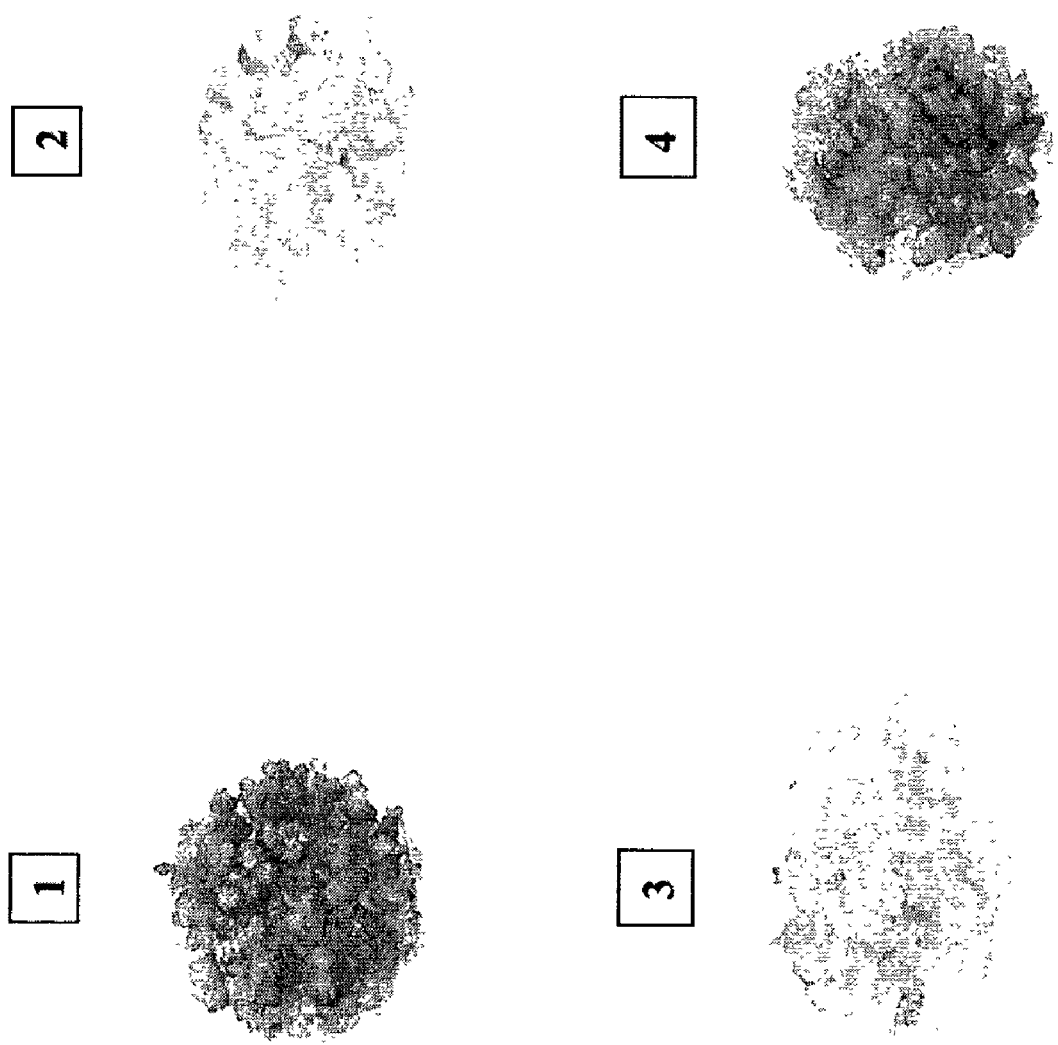
FIG. 21 depicts 4 embryonic calli transiently transformed with constructs including, in callus 1, GUS under control of the 35Sint promoter; in callus 2, GUS under control of the 35Sint promoter and DNA that produces double stranded GUS mRNA also under control of the 35Sint promoter; in callus 3, the same constructs as callus 2 and additionally RNase H-like protein under control of the 35Sint promoter; in callus 4, the same constructs as callus 2 and additionally DNA that produces RNase H-like protein mRNA under control of the 35Sint promoter; although the figures is not presented in color, the darker colored calli, calli 1 and 4 are blue while the lighter colored calli, calli 2 and 3 are pinkish tan was will apparent to one skiled in the art.

FIG. 16 shows a farwestern blot of His-S tagged sugarcane 14-3-3 probed with 35S labeled RNase H-like protein. A comparison of binding of labeled RNase H-like protein to the His-S tagged sugarcane 14-3-3 to the various controls indicates that the interaction is specific between the two proteins and also that it occurs in conditions approximating physiological conditions.

Example 16

HC-Pro Deletion Mutant and Interaction with RNase H-Like Protein

In order to better determine the region of SrMV HC-Pro responsible for interaction with the RNase H-like protein, a series of deletion mutants were created and their interaction was tested in yeast two-hybrid and farwestern blot assays as described above. The results of these experiments are summarized in Table 3 and indicate that the C terminal portion, including the last 10 kDa of the HC-Pro protein are required for interaction with the RNase H-like protein while the N terminal region up to 7 kDa is not necessary.

TABLE 3

| HC-Pro segment | Assay | Interaction |
| --- | --- | --- |
| Full length<br>←----------------→ | Yeast two-hybrid | +++ |
| Full length<br>←----------------→ | Farwestern | +++ |
| N 1.3 kDa deletion<br>←-------------→ | Yeast two-hybrid | +++ |
| N 7.0 kDa deletion<br>←----------→ | Yeast two-hybrid | +++ |
| C 10 kDa deletion<br>←----------→ | Farwestern | – |
| C 20 kDa deletion<br>←------→ | Farwestern | – |

+++ in yeast two-hybrid assays indicates that strong blue staining was seen in less than 30 minutes. +++ in farwestern assays indicates that binding was apparent after a short exposure time.

Example 17

Complete Cloning of Partial cDNA Prey Clones

Candidate clones whose corresponding protein sequences interact with SrMV HC-Pro or other bait proteins in vitro under physiological conditions may be completely cloned with 5' RACE procedures or other procedures known to the art.

Example 18

Production of Antiserum

To facilitate in vivo co-immunoprecipitation studies further outlined below, antisera recognizing SrMV HC-Pro or another protein involved in PTGS may be produced. Using a pET or PGEX expression plasmid construct as described above or another 6×his construct known to the art, one may produce 6×his-tagged SrMV HC-Pro or other protein in *E. coli*, purify the fusion protein as described above, and utilize the protein as an antigen with rabbits or other animals to produce polyclonal antisera. Similarly, SrMV P1 and host proteins may also be utilized to produce antisera, depending upon the potential utility of the resultant serum. Other antisera production techniques may also be used to produce polyclonal or, where useful, monoclonal antibodies.

Example 19

Transgenic Plant Studies

Because of its specific mode of action, the SrMV P1/HC-Pro and other proteins identified as involved in PTGS using the above two-hybrid and in vitro methods may target one or more factors that are expressed and functional in silenced tissue. This may be confirmed in planta. Because the cDNA library in the above examples was constructed from a plant harboring a PTGS-silenced SrMV coat protein sequence, and the plant is resistant to SrMV, one cannot readily utilize mechanical transmission of SrMV as a source of SrMV HC-Pro or other viral proteins in such plants, and thus may resort to transgenic methodologies.

Plant transformation studies demonstrate the feasibility of this approach. To date, SrMV HC-Pro transformants and SrMV P1/HC-Pro transformants have been confirmed via Southern and Northern analyses. The plants were produced via particle gun transformation of embryogenic callus, as previously described (Ingelbrecht et al., 1999). Three different plant transformation vectors have been constructed: (1) pIVING1023 which contains the SrMV P1/HC-Pro polyprotein sequence, in which SrMV HC-Pro may be expected to be cleaved out by the SrMV P1 protease in planta, (2) pIVING1002 which contains only the SrMV P1 sequence, and (3) pIVING991-1 which contains only the SrMV HC-Pro sequence. In the present example, two selectable markers for sugarcane transformation have been used, the nptII gene in combination with geneticin, and the bar gene for selection with bialaphos. Bialaphos selection may be used on bar transformed cells, and geneticin selection may be used on bar transgenic cells to select for second transformation events of previously transformed tissue. Other transformation mechanisms and selection systems known to the art may also be used. Such sequentially transformed plants may serve as a source of material for in planta studies.

In a further example, the transgenic plant #16 that was used as a source for construction of the prey cDNA library above, was utilized to generate embryogenic callus. Plant #16 was previously transformed with the bar gene, and in this example was transformed again with the SrMV P1-HC-Pro construct using geneticin selection. Because SrMV P1 has been described as an enhancer of the PTGS-inhibition by SrMV HC-Pro, the capsid message levels may be higher in SrMV P1-HC-Pro transformed #16 plants as compared to SrMV HC-Pro transformed #16 plants. In addition to having a system of modulated PTGS-suppression, these transgenic plants also allow verification in planta of the interactions between the viral proteins and the identified prey proteins, utilizing SrMV HC-Pro specific antiserum in standard co-immunoprecipitation methodologies.

Sequence homology of the isolated host proteins with known proteins, if present, may be used to postulate their biological function and whether or not they are involved in PTGS in a manner similar to that employed with the genes identified in mutagenesis studies of *Neurospora, C. elegans* and *Arabadopsis.*

One approach for determining functions of the isolated genes may be based on creating suppression phenotypes for these genes in sugarcane via genetic transformation. Efficient triggering of gene suppression can be achieved by simultaneous expression of sense and antisense constructs or constructs designed to produce dsRNA as demonstrated in tobacco, rice and *Arabadopsis* (Waterhouse et al., 1998; Smith et al., 2000; Chuang and Meyerowitz, 2000). See also FIG. 17 for depictions of the basic structure of DNA and resulting mRNA for such constructs. Such constructs may be created for each of the isolated host genes and introduced in plants that display PTGS of a capsid protein transgene, such as plant #16. The transformation methodologies described above can be followed to generate stably transformed plants. Alternatively, a protoplast-based system can be used in combination with electroporation or PEG-mediated transformation. Expression of the capsid protein will be analyzed and reversal of silencing may indicate that the PTGS mechanism in these transgenics is impaired and that the transformed host genes are involved in PTGS.

Example 20

In Planta Studies of HC-Pro and RNase H-Like Protein

Embryonic sugarcane calli were bombarded with various constructs according to the above examples in order to provide transient expression to verify the role of HN-Pro and RNase H-like protein in PTGS. Double stranded mRNA relating to the various proteins was generated using constructs such as those show in FIG. 17 inserted into the vector of FIG. 18.

FIG. 19 shows that GUS under a Ubi promoter alone is expressed in embryonic callus. Introduction of a double stranded GUS mRNA reduces its expression by activating PTGS of GUS mRNA. However expression is restored by both introducing SrMV P1-HC-Pro into the callus and by inducing PTGS of the RNase H-like protein using a double stranded mRNA of that protein. Average results for three separate experiments of this nature are depicted in FIG. 20 and show that statistically. significant results are consistently obtained. Overall, these experiments confirm that SrMV P1 and SrMV HC-Pro inhibits PTGS and that the RNase H-like protein is involved in effecting PTGS.

FIG. 21 illustrates the PTGS effect of the RNase H-like protein even more clearly. In these figures calli transiently transformed with GUS exhibit the protein. This protein production is severely disrupted by subsequent or simultaneous transformation with DNA that produces double stranded GUS mRNA, which triggers PTGS. PTGS is not turned off by the transformation of the GUS/double stranded GUS calli with RNase H. However, it is severely hampered by introduction of DNA that produces double stranded mRNA for RNase H-like protein, which induces PTGS of RNase H-like protein itself. These experiments demonstrate that the RNase-H like protein plays a role in PTGS. These results are summarized in Table 4.

TABLE 4

| Transformation Constructs | Callus Color |
|---|---|
| 35S-int/GUS | Blue |
| 35S-int/GUS + 35S-int/dsGUS | Not Blue |
| 35S-int/GUS + 35S-int/dsGUS + 35S-int/RNase H-like protein | Not Blue |
| 35S-int/GUS + 35S-int/dsGUS + 35S-int/ds RNase H-like protein | Blue |

All references mentioned in any portion of the foregoing specification are incorporated by reference herein.

What is claimed is:

1. A method of isolating nucleic acid encoding a plant polypeptide active in PTGS comprising the steps of:
   i) selecting a bait nucleic acid which encodes a bait protein suppressive of PTGS in plants;
   ii) preparing a cDNA prey library from a plant or plant tissue wherein the plant or plant tissue actively exhibits PTGS;
   iii) conducting a yeast two-hybrid assay with the bait and prey nucleic acids, wherein prey cDNA that yields a true positive yeast two-hybrid assay result encodes a polypeptide active in PTGS in the plant or plant tissue, wherein the bait nucleic acid comprises a sequence of SEQ. ID. NO. 1 or a sequence of a degenerate code homolog of SEQ. ID. NO. 1.

2. The method of claim 1 further comprising preparing a cDNA prey library from a monocot plant.

3. The method of claim 2 wherein the monocot is selected from the group consisting of sugarcane, corn, sorghum and rice.

4. The method of claim 1 further comprising the step of confirming interaction between the bait protein and the polypeptide active in PTGS using a farwestern blot assay.

5. The method of claim 1 further comprising the step of confirming interaction between the bait protein and the polypeptide active in PTGS using a pull down assay.

6. The method of claim 1 further comprising the step of confirming interaction between the bait protein and the polypeptide active in PTGS using an in planta assay.

7. The method of claim 6 wherein the in planta assay is conducted in embryonic calli of the plant.

8. An isolated nucleic acid molecule comprising a nucleic acid molecule having at least 85% identity with the nucleic acid sequence of SEQ. ID. NO. 1 and operable to encode a P1/Hc-Pro protein functional in reversina PTGS in a plant.

9. An isolated nucleic acid molecule comprising a nucleic acid molecule having the nucleic acid sequence of SEQ. ID. NO. 1 or the nucleic acid sequence of a degenerate code homolog of SEQ. ID. NO. 1.

* * * * *

UNITED STATES PATENT AND TRADEMARK OFFICE
CERTIFICATE OF CORRECTION

PATENT NO. : 7,001,739 B2
APPLICATION NO. : 10/226715
DATED : February 21, 2003
INVENTOR(S) : Mirkov et al.

It is certified that error appears in the above-identified patent and that said Letters Patent is hereby corrected as shown below:

Col. 41, lines 3-6. Please replace Claim 8 with the following amended paragraph:

8. An isolated nucleic acid molecule comprising a nucleic acid molecule having at least 85% identity with the nucleic acid sequence of SEQ.ID.NO. 1 and operable to encode a P1/Hc-Pro protein functional in ~~reversina~~ reversing PTGS in a plant.

Signed and Sealed this

Twenty-ninth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 7,001,739 B2
APPLICATION NO. : 10/226715
DATED : February 21, 2006
INVENTOR(S) : Mirkov et al.

It is certified that error appears in the above-identified patent and that said Letters Patent is hereby corrected as shown below:

Col. 41, lines 3-6. Please replace Claim 8 with the following amended paragraph:

8. An isolated nucleic acid molecule comprising a nucleic acid molecule having at least 85% identity with the nucleic acid sequence of SEQ.ID.NO. 1 and operable to encode a P1/Hc-Pro protein functional in ~~reversina~~ reversing PTGS in a plant.

This certificate supersedes Certificate of Correction issued August 29, 2006.

Signed and Sealed this

Tenth Day of October, 2006

JON W. DUDAS
*Director of the United States Patent and Trademark Office*